United States Patent
Majewski et al.

(10) Patent No.: US 12,059,486 B2
(45) Date of Patent: Aug. 13, 2024

(54) COSMETIC COMPOSITIONS

(71) Applicant: Rodan & Fields, LLC, San Francisco, CA (US)

(72) Inventors: George P. Majewski, San Francisco, CA (US); Christine Crane, San Francisco, CA (US); John Simon Craw, San Francisco, CA (US); Gabriele Di Fiore, San Francisco, CA (US); Dzung Q. Le, San Francisco, CA (US); Olga Dueva-Koganov, San Francisco, CA (US); Robert Bianchini, San Francisco, CA (US); Angela M. Rivera, San Francisco, CA (US)

(73) Assignee: Rodan &Fields, LLC, San Francisco, CA (US)

( * ) Notice: Subject to any disclaimer, the term of this patent is extended or adjusted under 35 U.S.C. 154(b) by 142 days.

(21) Appl. No.: 17/647,877

(22) Filed: Jan. 13, 2022

(65) Prior Publication Data
US 2022/0218574 A1     Jul. 14, 2022

Related U.S. Application Data

(60) Provisional application No. 63/136,722, filed on Jan. 13, 2021.

(51) Int. Cl.
*A61K 8/14*     (2006.01)
*A61K 8/34*     (2006.01)
(Continued)

(52) U.S. Cl.
CPC ............... *A61K 8/14* (2013.01); *A61K 8/345* (2013.01); *A61K 8/41* (2013.01); *A61K 8/44* (2013.01);
(Continued)

(58) Field of Classification Search
None
See application file for complete search history.

(56) References Cited

U.S. PATENT DOCUMENTS

| | | | |
|---|---|---|---|
| 9,314,527 B2 | 4/2016 | Cottrell et al. | |
| 2003/0124152 A1 | 7/2003 | Pang | |

(Continued)

FOREIGN PATENT DOCUMENTS

| | | | | |
|---|---|---|---|---|
| CN | 100393300 C | * | 6/2008 | ........... A61K 31/401 |
| TW | 201141522 A | | 12/2011 | |

(Continued)

OTHER PUBLICATIONS

Singh et al., Novel Vitamin E TPGS based docetaxel nanovesicle formulation for its safe and effective parenteral delivery: Toxicological, pharmacokinetic and pharmacodynamic evaluation, 2021, Journal of Liposome Research, 31(4), 365-380, DOI: 10.1080/08982104.2020.1835955 (Year: 2021).*

(Continued)

*Primary Examiner* — Ernst V Arnold
(74) *Attorney, Agent, or Firm* — Goodwin Procter LLP

(57) ABSTRACT

The compositions of various embodiments include a tocopherol phosphate mixture (TPM) comprising a liposome having a lipid bilayer and an internal aqueous compartment, a lipophilic ingredient, a polar solvent system, an alcohol, a base, and a water soluble phase, wherein the liposome is made of a tocopherol phosphate derivative, wherein the lipophilic ingredients are entrapped in the lipophilic bilayer of the liposome, and wherein a water soluble ingredient is dissolved in the water soluble phase and is in the internal compartment of the liposome. The methods include improving the look of skin particularly of the neck and décolletage, increasing expression of an extracellular matrix proteins in skin, improving a keloid scar in a subject, and improving (Continued)

aging skin. Additionally, methods for preparing the compositions are described herein.

20 Claims, 4 Drawing Sheets

(51) Int. Cl.
| | |
|---|---|
| *A61K 8/41* | (2006.01) |
| *A61K 8/44* | (2006.01) |
| *A61K 8/67* | (2006.01) |
| *A61K 8/73* | (2006.01) |
| *A61Q 19/08* | (2006.01) |

(52) U.S. Cl.
CPC .............. *A61K 8/671* (2013.01); *A61K 8/676* (2013.01); *A61K 8/678* (2013.01); *A61K 8/73* (2013.01); *A61Q 19/08* (2013.01); *A61K 2800/805* (2013.01)

(56) References Cited

U.S. PATENT DOCUMENTS

| | | | |
|---|---|---|---|
| 2006/0281716 | A1 | 12/2006 | West et al. |
| 2007/0020220 | A1 | 1/2007 | Osborne |
| 2009/0098171 | A1 | 4/2009 | Alard et al. |
| 2009/0104258 | A1* | 4/2009 | Dumas ..................... A61K 8/14 514/100 |
| 2009/0186856 | A1 | 7/2009 | West et al. |
| 2010/0261670 | A1 | 10/2010 | West et al. |
| 2011/0003774 | A1 | 1/2011 | West et al. |
| 2011/0244023 | A1 | 10/2011 | Cottrell et al. |
| 2012/0202780 | A1 | 8/2012 | Gavin et al. |
| 2012/0283233 | A1 | 11/2012 | Gavin et al. |
| 2014/0072617 | A1* | 3/2014 | Dumas ..................... A61K 8/14 514/100 |
| 2017/0172863 | A1 | 6/2017 | Richard |
| 2019/0298834 | A1 | 10/2019 | Gavin et al. |

FOREIGN PATENT DOCUMENTS

| | | | |
|---|---|---|---|
| WO | 2002026238 | A1 | 4/2002 |
| WO | 2002040033 | A1 | 5/2002 |
| WO | 2002040034 | A1 | 5/2002 |
| WO | 2003011303 | A1 | 2/2003 |
| WO | 2003049774 | A1 | 6/2003 |
| WO | 2004014432 | A1 | 2/2004 |
| WO | 2004064831 | A1 | 8/2004 |
| WO | 2004091636 | A1 | 10/2004 |
| WO | 2004092186 | A1 | 10/2004 |
| WO | 2004092187 | A1 | 10/2004 |
| WO | 2005124563 | A2 | 12/2005 |
| WO | 2006012692 | A1 | 2/2006 |
| WO | 2006092024 | A1 | 9/2006 |
| WO | 2006092025 | A1 | 9/2006 |
| WO | 2006133506 | A1 | 12/2006 |
| WO | 2007070981 | A1 | 6/2007 |
| WO | 2011075775 | A1 | 6/2011 |
| WO | 2011094814 | A1 | 8/2011 |
| WO | 2011094822 | A1 | 8/2011 |
| WO | 2011120070 | A1 | 10/2011 |
| WO | 2012122586 | A1 | 9/2012 |
| WO | 2017096427 | A1 | 6/2017 |
| WO | 2018102888 | A1 | 6/2018 |
| WO | 2018112512 | A1 | 6/2018 |
| WO | 2018225229 | A1 | 12/2018 |
| WO | 2020217231 | A2 | 10/2020 |

OTHER PUBLICATIONS

Gavin et al., Tocopheryl phosphate mixture (TPM) as a novel lipid-based transdermal drug delivery carrier: formulation and evaluation, 2017, Drug Delivery and Translational Research, 7, 53-65, DOI: 10.1007/s13346-016-0331-x (Year: 2017).*

Mohammed et al., In Vitro-In Vivo Correlation in Skin Permeation, 2014, Pharmaceutical Research, 31, 364-400, DOI: 10.1007/s11095-013-1169-2 (Year: 2014).*

Truchuelo et al., Assessment of the efficacy and tolerance of a new combination of retinoids and depigmenting agents in the treatment of melasma, 2014, J Cosmet Dermatol, 13(4), 261-268, DOI: 10.1111/jocd.12110 (Year: 2014).*

Mccormack et al., A Review of Pterostilbene Antioxidant Activity and Disease Modification, 2013, Oxidative Medicine and Cellular Longevity, 2013, DOI: 10.1155/2013/575482 (Year: 2013).*

Kumar et al., Pharmaceutical importance, physico-chemical analysis and utilisation of Indian sandalwood (Santalum album Linn.) seed oil, 2019, Journal of Pharmacognosy and Phytochemistry, 8(1), 2587-2592, E-ISSN: 2278-4136 (Year: 2019).*

PubChem "Ximenynic acid" (https://pubchem.ncbi.nlm.nih.gov/compound/5312688; accessed May 31, 2023) (Year: 2023).*

Cosmetic Ingredient Review, Final report of the amended safety assessment of Glyceryl Laurate, Glyceryl Laurate SE, Glyceryl Laurate/Oleate, Glyceryl Adipate, Glyceryl Alginate . . . ,2004, Ing J Toxicol, 23, 55-94, DOI: 10.1080/10915810490499064 (Year: 2004).*

Serrano et al., Phosphatidylcholine liposomes as carriers to improve topical ascorbic acid treatment of skin disorders, 2015, Clinical , Cosmetic and Investigational Dermatology, 8, 591-5991, DOI: 10.2147/CCID.S90781 (Year: 2015).*

Abu-Huwaji et al., Formulation and In Vitro Evaluation of Xanthan Gum or Carbopol 934-Based Mucoadhesive Patches, Loaded with Nicotine, 2011, AAPS PharmSciTech, 12, 21-27, DOI: 10.1208/s12249-010-9534-5 (Year: 2011).*

Mozafari et al. (International Journal of Pharmaceutics 2017;528:381-382) (Year: 2017).*

International Search Report and Written Opinion for International PCT Application No. PCT/US2022/070171 dated Jun. 8, 2022.

Carrino et al., "Age-Related Changes in the Proteoglycans of Human Skin. Specific Cleavage of Decorin to Yield a Major Catabolic Fragment in Adult Skin," J Biol. Chem. (May 9, 2003) 278(19): pp. 17566-17572.

Carrino et al., "Age-Related Differences in Human Skin Proteoglycans," Glycobiology (Feb. 2011) 21(2): pp. 257-268.

Gad, "Anti-Aging Effects of L-Arginine," J. Adv. Res., Jul. 2010, 1(3): pp. 169-177.

Gavin et al., "Tocopheryl Phosphate Mixture (TPM) as a Novel Lipid-Based Transdermal Drug Delivery Carrier: Formulation and Evaluation," Drug Deliv. and Transl. Res. (2017) 7:53-65.

Kahari et al., "Differential Regulation of Decorin and Biglycan Gene Expression by Dexamethasone and Retinoic Acid in Cultured Human Skin Fibroblasts," Journal of Investigative Dermatology (Apr. 1995), 104(4): pp. 503-508.

Li et al., "Age-Dependent Alterations of Decorin Glycosaminoglycans in Human Skin," Sci. Rep. 2013; 3:2422, pp. 1-8.

Nomura, "Structural Change in Decorin with Skin Aging," Connect Tissue Res. (2006); 47(5): pp. 249-255.

Pelle et al., "An In Vitro Model to Test Relative Antioxidant Potential: Ultraviolet-Induced Lipid Peroxidation in Liposomes," Arch Biochem & Biophys. (Dec. 1990) 283(2): pp. 234-240.

Yoshida et al., "Quantitative Histological Analyses and Transcriptional Profiling Reveal Structural and Molecular Changes of the Dermal Extracellular Matrix in Cellulite," J. Dermatol Sci. (Oct. 1, 2018) 92(1): pp. 6-9.

* cited by examiner

COSMETIC COMPOSITIONS

PRIORITY CLAIM

This application claims the benefit of priority of U.S. Provisional Application No. 63/136,722 filed Jan. 13, 2021, the contents of which are hereby incorporated by reference.

SUMMARY

Embodiments disclosed herein are directed to tocopherol phosphate mixture (TPM) liposomal compositions comprising a liposome, made of a mixture of tocopherol phosphate derivatives, having a lipid bilayer and an internal compartment, a polar solvent system containing a polar solvent 1, a polar solvent 2, and a $C_1$-$C_6$ alcohol, a neutralizing base, and a water soluble phase, wherein one or more lipophilic ingredients is entrapped in the lipid bilayer of the liposome, and one or more water soluble ingredients is dissolved in the water soluble phase in the internal compartment of the liposome, and wherein the TPM liposomal composition has a pH of about 4.5 to about 5.

Embodiments disclosed herein are directed to topical final formulations comprising about 0.1% to about 40% of a TPM liposomal composition by weight of the topical final formulation, an additive, water, and a cosmetically acceptable excipient.

Embodiments are directed to methods of improving the look of skin in a human subject in need thereof comprising topically administering to the skin of the subject a topical final formulation comprising about 0.1% to about 40% of a TPM liposomal composition by weight of the topical final formulation, an additive, water, and a cosmetically acceptable excipient. In embodiments the skin is the neck or décolletage.

Embodiments are directed to methods of increasing expression of an extracellular matrix protein in skin of a subject in need thereof comprising administering a topical final formulation comprising about 0.1% to about 40% of a TPM liposomal composition by weight of the topical final formulation, an additive, water, and a cosmetically acceptable excipient.

Embodiments are directed to methods of improving a keloid scar in a subject in need thereof comprising topically administering a topical final formulation comprising about 0.1% to about 40% of a TPM liposomal composition by weight of the topical final formulation, an additive, water, and a cosmetically acceptable excipient.

Embodiments are directed to methods of improving the appearance of aged skin in a subject in need thereof comprising topically administering a topical final formulation comprising about 0.1% to about 40% of a TPM liposomal composition by weight of the topical final formulation, an additive, water, and a cosmetically acceptable excipient.

Embodiments are directed to methods of improving the appearance of various keratinous fibers in a subject in need thereof comprising topically administering a topical final formulation comprising about 0.1% to about 40% of a TPM liposomal composition by weight of the topical final formulation, an additive, water, and a cosmetically acceptable excipient.

Embodiments are directed to methods of improving the contour of the neck or jawline in a subject in need thereof comprising topically administering a topical final formulation comprising about 0.1% to about 40% of a TPM liposomal composition by weight of the topical final formulation, an additive, water, and a cosmetically acceptable excipient.

Embodiments are directed to methods of decreasing the appearance of cellulite in a subject in need thereof comprising topically administering a topical final formulation comprising about 0.1% to about 40% of a TPM liposomal composition by weight of the topical final formulation, an additive, water, and a cosmetically acceptable excipient.

Embodiments are directed to methods of increasing expression of an extracellular matrix protein in a model system based on a cell-based assay using adult human dermal fibroblasts or in a 3-dimensional reconstructed skin model comprising administering a TPM liposomal composition comprising a liposome, made of a mixture of tocopherol phosphate derivatives, having a lipid bilayer and an internal compartment, a polar solvent system containing a polar solvent 1, a polar solvent 2, and a $C_1$-$C_6$ alcohol, a neutralizing base, and a water soluble phase, wherein one or more lipophilic ingredients is entrapped in the lipid bilayer of the liposome, and one or more water soluble ingredients is dissolved in the water soluble phase in the internal compartment of the liposome, and wherein the TPM liposomal composition has a pH of about 4.5 to about 5.

Embodiments are directed to methods for preparing a TPM liposomal composition comprising:

a) mixing a lipophilic ingredient with a polar solvent system (such as dimethyl isosorbide (DMI) and pentylene glycol) and heating the resulting mixture to a temperature between about 60° C. to about 65° C.;

b) adding a tocopherol phosphate derivative ingredient to the mixture from step a) once temperature reaches about 57.9° C. to about 61° C., heating and maintaining the temperature of the resulting mixture to between about 57.9° C. to about 61° C. until all contents melted;

c) cooling the mixture from step b) to a temperature between about 32° C. to about 35° C., adding one or more lipophilic ingredients and ethanol into the cooled mixture, and mixing the mixture until complete dissolution to form Phase A;

d) mixing, in a separate container, one or more water soluble ingredients, and water thoroughly and keeping the resulting mixture at a temperature between about 38° C. to about 40° C. to form Phase B;

e) adding Phase A into Phase B and mixing the resulting mixture at a temperature between about 38° C. to about 40° C. for at least 20 minutes;

f) adding a neutralizing base such as tromethamine, g) dispersing a gelling agent, such as xanthan gum, into a humectant, such as glycerin, to form Phase C and mixing into solution of step e), and h) turning off the heat to the mixture of step g) and stirring the mixture until the temperature of the mixture reaches room temperature. Embodiments also include adding the TPM liposomal composition mixture to a final formulation at about 0.1% to about 40% by weight of the topical final formulation, wherein the final formulation additionally includes an additive, water, and a cosmetically acceptable excipient.

BRIEF DESCRIPTION OF THE DRAWINGS

For a fuller understanding of the nature and advantages of the present embodiments, reference should be made to the following detailed description taken in connection with the accompanying drawings, in which.

DETAILED DESCRIPTION

Figure 1A:
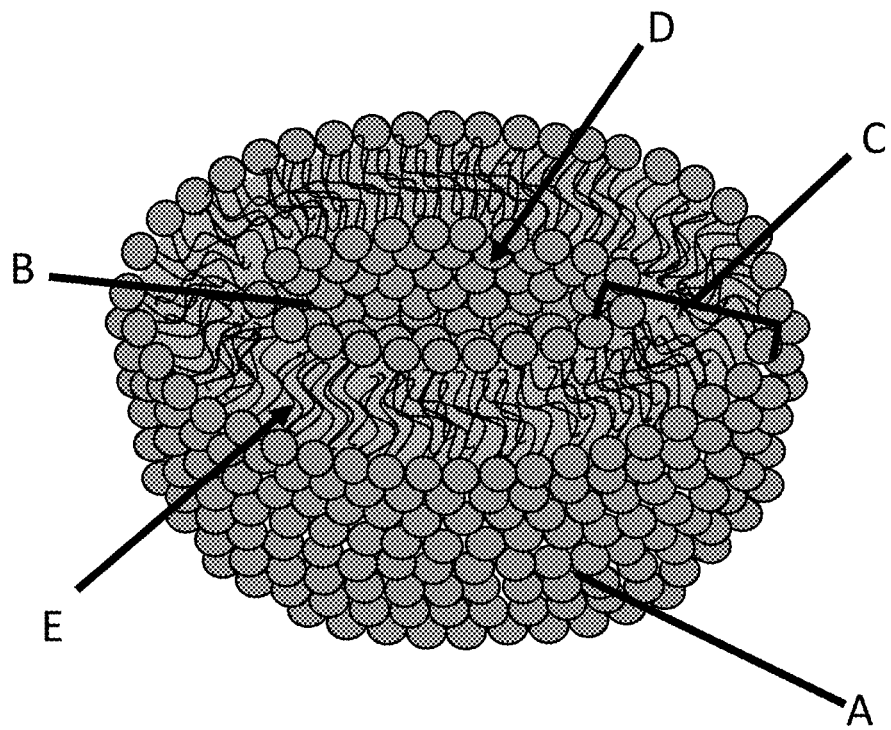
FIG. 1A is a three-dimensional schematic of a liposome showing the compartments as described herein.

Consumers believe that modern life is damaging to the skin. What is referred to as "tech neck" has become a growing concern for consumers, affecting women who are younger than those traditionally experiencing issues with their neck skin. Accordingly, to keep skin looking young and healthy, women need to be as consistent with their neck and chest routine as they are with their face.

The epidermis, the outer layer of the skin, protects from the environment and resists topically applied substances. A range of substances have been developed which penetrate the skin in a variety of methods. For example, hydroxosomes penetrate the epidermis and dermis of the skin transappendageally (through hair follicle and sweat gland); nanosomes, nanoemulsions, or liposomes penetrate the epidermis and dermis of the skin transcellularly (passing from cell to cell, through adjacent cell membranes), and humectant hydration penetrates the epidermis and dermis of the skin paracellularly (passing through the intercellular space between cells).

The thickness of the epidermis and dermis of the skin is quite different over the entire body. Importantly, the epidermis of the neck and décolletage is about two fold the thickness of the eyelid, however, the dermis of the skin of the neck is thinner than most other facial areas. Accordingly, delivering cosmetic actives to the neck skin area maybe challenging due to the epidermal thickness. The neck and décolletage dermis is thinner than most facial skin and with age the structure may be more prone to sagging and deep wrinkles as the connective tissue weakens. Fat deposits in the hypodermis (located below the dermis) are likely to protrude through the dermis/epidermis for a stronger visible impact, creating a cellulite-like effect.

A capable delivery system can be employed with cosmetic ingredients which can support the extracellular matrix (ECM) constituents (i.e. collagen and elastin) and induce triglyceride (fat) metabolism (cyclic AMP).

As described in further detail herein, alpha-tocopheryl phosphate (TP) and di-alpha-tocopheryl phosphate (T2P) are two phosphorylated forms of vitamin E which form tocopheryl phosphate mixture (TPM), which produce small particle size micelles or vesicles. TPM is useful delivery carrier for agents used to improve skin quality and/or which have anti-aging qualities and/or anti-cellulite properties.

Embodiments described herein are directed to TPM liposomal compositions and topical final formulations containing said TPM liposomal compositions which effectively penetrate the skin, including the skin of the neck and décolletage, and to deliver cosmetic agents to improve the look and feel of the skin.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 wt % to 8 wt % is stated, it is intended that 2 wt %, 3 wt %, 4 wt %, 5 wt %, 6 wt %, and 7 wt % are also explicitly disclosed, as well as the range of values greater than or equal to 1 wt % and the range of values less than or equal to 8 wt %.

All percentages, parts and ratios are based upon the total weight of the formulations and compositions and all measurements made are at about 25° C., unless otherwise specified.

The singular forms "a," "an," and "the" include plural referents unless the context clearly dictates otherwise. Thus, for example, reference to "a polymer" includes a single polymer as well as two or more of the same or different polymers; reference to "an excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. Furthermore, the phrases "less than about" a value or "greater than about" a value should be understood in view of the definition of the term "about" provided herein.

The terms "administer," "administering" or "administration" as used herein refer to directly administering a composition, including an agent of interest, to the skin of a subject.

The term "excipients" as used herein encompasses carriers and diluents, meaning a material, composition or vehicle, such as a liquid or solid filler, diluent, excipient, solvent or encapsulating material involved in carrying or transporting a cosmetic or other agent across a tissue layer such as the stratum corneum or stratum spinosum.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed subject matter. In some embodiments or claims where the term comprising is used as the transition phrase, such embodiments can also be envisioned with replacement of the term "comprising" with the terms "consisting of" or "consisting essentially of."

The term "cosmetic" means an agent utilized, and/or intended to be applied to the human body for cleansing, beautifying, promoting attractiveness, altering the appearance of the skin, or any combination thereof.

The term "keratinous fiber" as used herein refers to any tissue which contain keratin as a fibrous structural protein, including, but not limited to, skin, hair, and nails.

Figure 1B:
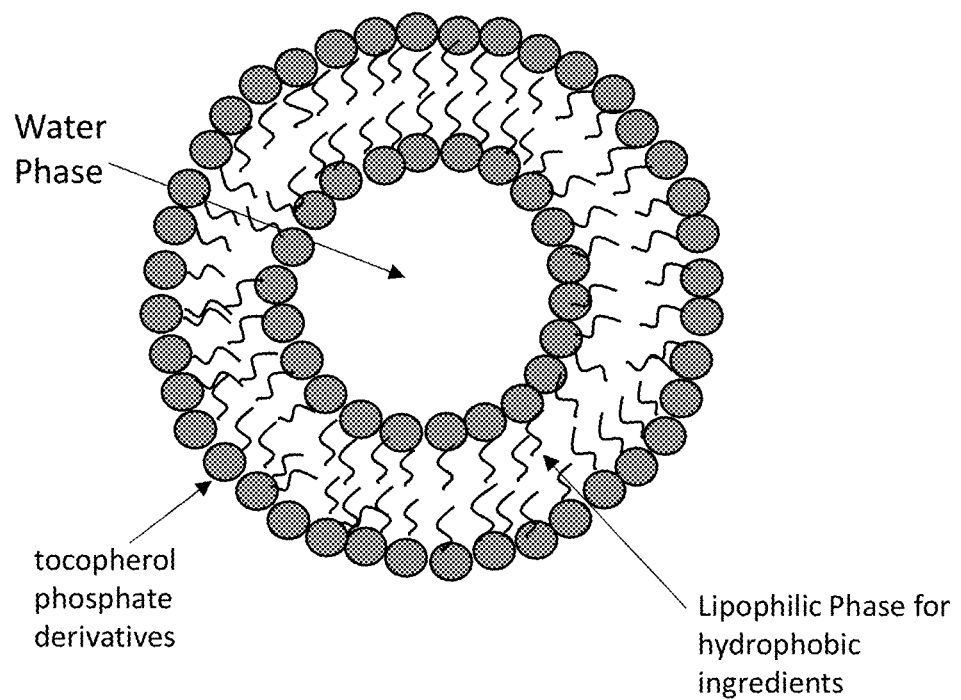
FIG. 1B is a two-dimensional schematic of the same.

The term "liposome" as used herein interchangeably with "vesicle" means an artificial vesicle composed of one or more concentric phospholipid-like bilayers (as provided in FIG. 1A or 1B), used especially to deliver microscopic substances (such as cosmetic additives or other additives) to the skin. The hydrophobic tocopherol phosphate derivative/vitamin E portions associate in an aqueous environment to form closed, spherical bilayers encapsulating hydrophobic components of interest within the bilayer compartment. The enclosed aqueous volume or water phase is within the internal compartment where the hydrophilic ingredients of interest are dissolved.

The phrase "cosmetically acceptable" is employed herein to refer to those agents of interest/compounds, salts, compositions, dosage forms, etc, which are suitable for use in contact with the tissues of human beings and/or other mammals without excessive toxicity, irritation, allergic response, or other problem or complication, commensurate with a reasonable benefit/risk ratio.

The term "upregulation" as used herein refers to the process of increasing the response to a stimulus. Specifically, it refers to the increase in a cellular response to a molecular stimulus due to increase in the number of receptors on the cell surface. In the biological context of organisms' production of gene products, upregulation is the process by which a cell increases the quantity of a cellular component, such as RNA or protein, in response to an external stimulus.

The term "subject" may be taken to mean any living organism which may be administered compounds or compositions provided for herein. As such, the term "subject" may comprise, but is not limited to, any non-human mammal, primate or human. In some embodiments, the subject is an adult, child or infant. In some embodiments, the subject is a human.

As used herein, the term "topically" and "topical" refers to application of the compositions described herein to the surface of the skin, mucosal cells, tissues, and/or keratinous fibers.

The use of "TPM" refers to a mixture of alpha-tocopheryl phosphate (TP) and di-alpha-tocopheryl phosphate (T2P) which are two phosphorylated forms of vitamin E which form tocopheryl phosphate mixture (TPM). TPM acts as a liposome to encapsulate both hydrophobic and hydrophilic molecules at high efficiency. The addition of TPM to formulations of a number of different actives results in enhanced uptake into, and through, the skin. Unlike nanoparticle delivery systems composed of biologically inert phospholipids or surfactants, TPM itself has attractive properties beyond simply agent delivery, namely the ability to reduce irritation of adverse effects brought about by the delivery of irritating or sensitizing cosmetic agents.

The term "treating" as used herein refers generally to include the administration of a compound or composition which reduces a scar, decreases the appearance of cellulite, or enhances the texture, appearance, color, sensation, or hydration of the intended tissue treatment area of the tissue surface in a subject relative to a subject not receiving the compound or composition. This can include reversing, reducing, or arresting the unwanted symptoms, to improve or stabilize a subject's skin.

In any of the embodiments described herein, the compositions are cosmetic compositions and are for cosmetic use. In any of the embodiments described herein, the compositions are not pharmaceutical compositions and are not for pharmaceutical use.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

TPM Liposomal Compositions

Embodiments disclosed herein are directed to a TPM liposomal composition comprising: a liposome, made of a mixture of tocopherol phosphate derivatives, having a lipid bilayer and an internal compartment, a polar solvent system containing a polar solvent 1, a polar solvent 2, and a $C_1$-$C_6$ alcohol, a neutralizing base, and a water soluble phase, wherein one or more lipophilic ingredients is entrapped in the lipid bilayer of the liposome, and one or more water soluble ingredients is dissolved in the water soluble phase in the internal compartment of the liposome, and wherein the TPM liposomal composition has a pH of about 4.5 to about 5. In certain embodiments, water soluble components of the polar solvent system will be in the water soluble phase and may diffuse out of the liposome. In certain embodiments, water soluble $C_1$-$C_6$ alcohols will be in the water soluble phase and may diffuse out of the liposome. In certain embodiments, the neutralizing base will be in the water soluble phase.

In certain embodiments, the liposome is a multilamellar vesicle (MLV), a small unilamellar vesicle (SUV), or a large unilamellar vesicle (LUV). Multilamellar vesicles (MLV) have several lipid bilayers, i.e. liposomes within liposomes. Unilamellar vesicles, SUV or LUV, have a single lipid bilayer.

Without being bound to any particular theory, the liposomes can be used to facilitate topical delivery and stability of components of the TPM liposomal composition. In some embodiments, the liposomes have a particle size range of about 100 nm to about 1000 nm, with a median particle size of about 300 nm to about 700 nm. In some embodiments, the particle size is determined by Method A as described herein.

In certain embodiments, the polar solvent system, which comprises a polar solvent 1, a polar solvent 2, and a $C_1$-$C_6$ alcohol, is present in an amount of about 15% to about 20% by weight of the TPM liposomal composition. In certain embodiments, the polar solvent system is present in an amount of about 18.08% by weight of the TPM liposomal composition. In certain embodiments, the polar solvent system is present in an amount of about 16% by weight of the TPM liposomal composition.

In some embodiments, the $C_1$-$C_6$ alcohol is selected from the group consisting of methanol, ethanol, 1-propanol, and isopropanol. In preferred embodiments, the $C_1$-$C_6$ alcohol is ethanol.

In some embodiments, the $C_1$-$C_6$ alcohol is present in an amount of about 5% to about 10% by weight of the TPM liposomal composition. In preferred embodiments, the $C_1$-$C_6$ alcohol is at about 7% by weight of the TPM liposomal composition. In preferred embodiments, the $C_1$-$C_6$ alcohol is at about 8% by weight of the TPM liposomal composition. Without being bound by theory, $C_1$-$C_6$ alcohol within the disclosed ranges is required to get efficient formation of the liposomes without precipitation within the composition.

In certain embodiments, the polar solvent 1 and the polar solvent 2 of the polar solvent system is present in an amount of about 8% to about 12% by weight of the TPM liposomal composition. In certain embodiments, the polar solvent system is present in an amount of about 10.08% by weight of the TPM liposomal composition. In preferred embodiments, the polar solvent system is present in an amount of about 9% by weight of the TPM liposomal composition.

In some embodiments, the polar solvent 1 and the polar solvent 2 of the polar solvent system are selected from the group consisting of a polyol, a mono-alkyl isosorbide ether, di-alkyl isosorbide ether, and combinations thereof. In some embodiments, the polyol is pentylene glycol. In some embodiments, the di-alkyl isosorbide ether is dimethyl isosorbide.

In preferred embodiments, the polar solvent 1 is pentylene glycol (PG). In preferred embodiments, the polar solvent 2 is dimethyl isosorbide (DMI). In certain embodiments, the ratio of polar solvent 1 to polar solvent 2 is selected from the group consisting of 3:2, 2.5:1.5, 2:1, 2:1.5, 1.5:1, and 1:1. In certain embodiments, the ratio of polar solvent 1 to polar solvent 2 is 2.27:1. In certain embodiments, the ratio of polar solvent 1 to polar solvent 2 is 1.47:1. In certain embodiments, the ratio of polar solvent 1 to polar solvent 2 is 2:1.

In certain embodiments, the ratio of the $C_1$-$C_6$ alcohol to the polar solvent 1 to the polar solvent 2 ($C_1$-$C_6$ alcohol: polar solvent 1:polar solvent 2) is selected from the group consisting of 4:4:1, 3:2:1, 2.59:2.27:1, 2.3:2:1, 2:1.5:1, 1.71:1.47:1, and 1:1:1. In preferred embodiments, the ratio of the $C_1$-$C_6$ alcohol to the polar solvent 1 to the polar solvent 2 is 2.59:2.27:1. In certain embodiments, the ratio of the $C_1$-$C_6$ alcohol to the polar solvent 1 to the polar solvent 2 is 1.71:1.47:1. In preferred embodiments, the ratio of the $C_1$-$C_6$ alcohol to the polar solvent 1 to the polar solvent 2 is 2.3:2:1.

In certain embodiments, the polar solvent 1 is present in an amount of about 5% to about 10% by weight of the TPM liposomal composition. In certain embodiments, the polar solvent 1 is present in an amount of about 6% to about 7.5% by weight of the TPM liposomal composition. In preferred embodiments, the polar solvent 1 is present in an amount of about 6% by weight of the TPM liposomal composition. In preferred embodiments, the polar solvent 1 is present in an amount of about 7% by weight of the TPM liposomal composition.

In certain embodiments, the polar solvent 2 is present in an amount of about 2% to about 6% by weight of the TPM liposomal composition. In certain embodiments, the polar solvent 2 is present in an amount of about 3% to about 4% by weight of the TPM liposomal composition. In preferred embodiments, the polar solvent 2 is present in an amount of about 3% by weight of the TPM liposomal composition. In preferred embodiments, the polar solvent 2 is present in an amount of about 3.08% by weight of the TPM liposomal composition.

In most preferred embodiments, the solvent system comprises about 7% pentylene glycol, about 3.08% dimethyl isosorbide, and about 8% ethanol.

In most preferred embodiments, the solvent system comprises about 6% pentylene glycol, about 3% dimethyl isosorbide, and about 7% ethanol.

In certain embodiments, the mixture of tocopherol phosphate derivatives is selected from the group consisting of alpha tocopherol phosphate derivatives, beta tocopherol phosphate derivatives, gamma tocopherol phosphate derivatives, and delta tocopherol phosphate derivatives in enantiomeric and racemic forms. In certain embodiments, the mixture of tocopherol phosphate derivatives is a mono-tocopheryl phosphate derivative and a di-tocopheryl phosphate derivative. In certain embodiments, the mixture of tocopherol phosphate derivatives comprises an alpha-tocopheryl phosphate (TP) and a di-alpha-tocopheryl phosphate (T2P). In certain embodiments, the mixture of alpha-tocopheryl phosphate (TP) and a di-alpha-tocopheryl phosphate (T2P), also known as TPM, the ratio of TP:T2P is in a range of about 4:1 to about 1:1. In certain embodiments, the ratio of TP:T2P is selected from the group consisting of about 1.25:1, about 1.75:1, about 2.5:1, and about 3.5:1.

In certain embodiments, the mixture of tocopherol phosphate derivatives is present in an amount of about 1.5% to about 5% by weight of the TPM liposomal composition. In certain embodiments, the mixture of tocopherol phosphate derivatives is present in an amount of about 2.5% by weight of the TPM liposomal composition. In certain embodiments, the mixture of tocopherol phosphate derivatives is present in an amount of about 2.7% by weight of the TPM liposomal composition. In certain embodiments, alpha-tocopheryl phosphate (TP) is in an amount of about 0.75% to about 1.05% by weight of the TPM liposomal composition or about 2.5% to about 3.5% by weight of the TPM liposomal composition. In certain embodiments, di-alpha-tocopheryl phosphate (T2P) is in an amount of about 0.3% to about 0.6% by weight of the TPM liposomal composition or about 1% to about 2% by weight of the TPM liposomal composition.

In certain embodiments, the one or more lipophilic ingredients (which may also be referred to as the hydrophobic ingredients) is selected from the group consisting of a hydrophobically modified amino acid, a hydrophobically modified vitamin, a retinoid, a resveratrol derivative, a fatty acid, a fatty ester, and combinations thereof. In certain embodiments, the one or more lipophilic ingredients includes lipid soluble ingredients dissolved in fatty acids or fatty acid esters. In some embodiments, the hydrophobically modified amino acid is hydrophobically modified proline. In some embodiments, the hydrophobically modified amino acid is dipalmitoyl hydroxyproline. In some embodiments, the hydrophobically modified vitamin is a hydrophobically modified ascorbic acid. In some embodiments, the hydrophobically modified ascorbic acid is 3-O-cetyl ascorbic acid. In some embodiments, the retinoid is selected from the group consisting of retinaldehyde, ester of retinoic acid, hydroxypinacolone retinoate, retinyl palmitate, alitretinoin (9-cis-retinoic acid), tretinoin (all-trans-retinoic acid), isotretinoin (13-cis-retinoic acid), etretinate, acitretin, adapalene, bexarotene, tazarotene, and derivatives and combinations thereof. In some embodiments, the retinoid is hydroxypinacolone retinoate. In some embodiments, the one or more lipophilic ingredients is a blend of pterostilbene (resveratrol dimethyl ether) and xymenynic acid dissolved in glyceryl linoleate and glyceryl linolenate.

In certain embodiments, the one or more lipophilic ingredients is present in an amount of about 0.1% to about 5% by weight of the TPM liposomal composition. In certain embodiments, the one or more lipophilic ingredients is present in an amount of about 0.1% to about 1% by weight of the TPM liposomal composition. In some embodiments, the one or more lipophilic ingredients is present in an amount of about 0.12% by weight of the TPM liposomal composition. In some embodiments, the one or more lipophilic ingredients are present in an amount of about 0.5% by weight of the TPM liposomal composition. In some embodiments, the one or more lipophilic ingredients is present in an amount of about 0.62% by weight of the TPM liposomal composition. In some embodiments, the one or more lipophilic ingredients is present in an amount of about 1.0% by weight of the TPM liposomal composition. In some embodiments, the one or more lipophilic ingredients is present in an amount of about 1.5% by weight of the TPM liposomal composition. In some embodiments, the one or more lipophilic ingredients is present in an amount of about 5% by weight of the TPM liposomal composition.

In certain embodiments, the neutralizing base is an organic base. In certain embodiments, the organic base is selected from the group consisting of tromethamine, L-arginine, niacinamide, and combinations thereof. In preferred embodiments, the organic base is tromethamine. In certain embodiments, the neutralizing base is an inorganic base. In preferred embodiments, the inorganic base is sodium hydroxide (NaOH).

In some embodiments, the base is present in an amount of about 0.1% to about 1% by weight of the TPM liposomal composition. In some embodiments, the base is present in an amount of about 0.2% by weight of the TPM liposomal composition. In some embodiments, the base is present in an amount of about 0.3% by weight of the TPM liposomal composition.

In certain embodiments, the water soluble phase is present in an amount of about 70% to 85% by weight of the TPM liposomal composition. In certain embodiments, the water soluble phase comprises water in an amount of about 82.8% by weight of the TPM liposomal composition. In certain embodiments, the water soluble phase comprises water in an amount of about 77% by weight of the TPM liposomal composition. In certain embodiments, the water soluble phase comprises water in an amount of about 76% by weight of the TPM liposomal composition. In certain embodiments, the water soluble phase comprises water in an amount of about 75% by weight of the TPM liposomal composition. In certain embodiments, the water soluble phase comprises water in an amount of about 74% by weight of the TPM liposomal composition. In certain embodiments, the water soluble phase comprises water in an amount of about 73% by weight of the TPM liposomal composition.

In certain embodiments, the one or more water soluble ingredients is a water soluble amino acid, a water soluble vitamin, protein, xanthine, or combinations thereof. In some embodiments, the water soluble amino acid is selected from the group consisting of arginine, histidine, glycine, proline, and combinations thereof. In some embodiments, the water soluble amino acid is L-arginine. In some embodiments, the water soluble vitamin is selected from the group consisting of niacinamide, 3-O-ethyl ascorbic acid, vitamin C, and combinations thereof. In some embodiments, the water soluble protein is selected from the group consisting of, carnosine, dipeptide-2, tetrapeptide-21, tripeptide-3, tetrapeptide-4, copper tetrapeptide, acetyl dipeptide-1 cetyl ester, and combinations thereof. In some embodiments, the water soluble ingredient includes butylene glycol, sorbitan laurate, hydroxyethylcellulose, and acetyl dipeptide-1 cetyl ester. In some embodiments, the xanthine is selected from the group consisting of methylxanthine, 1,3-dimethylxanthine (also known as theophylline), caffeine, and combinations thereof.

In some embodiments, the one or more water soluble ingredients is present in an amount of about 0.1% to about 4% by weight of the TPM liposomal composition. In some embodiments, the one or more water soluble ingredients is present in an amount of about 0.5% by weight of the TPM liposomal composition. In some embodiments, the one or more water soluble ingredients is present in an amount of about 1.0% by weight of the TPM liposomal composition. In some embodiments, the one or more water soluble ingredients is present in an amount of about 2.5% by weight of the TPM liposomal composition.

In some embodiments, the TPM liposomal composition further comprises a humectant. In some embodiments, the humectant is selected from the group consisting of glycerin, diglycerin, betaine, diols, propylene glycol, butylene glycol, pentylene glycol, propanediol, 1,2-hexanediol, D-ribose, glucose, sorbitol, dextrose, urea, 2-Pyrrolidone-5-Carboxylic Acid and related salts, sea salt, inorganic salts of citric acid, inorganic salts of lactic acid, ectoin, lactic acid, betaine, glycolic acid, lactobionic acid, and any combination thereof. In some embodiments, the humectant is glycerin. In certain embodiments, the humectant is in the water soluble phase.

In some embodiments, the humectant is present in an amount of about 0.1% to about 5% by weight of the TPM liposomal composition. In some embodiments, the humectant is present in an amount of about 2.0% by weight of the TPM liposomal composition.

In some embodiments, the TPM liposomal composition further comprises a gelling agent. In some embodiments, the gelling agent is in the water phase. In some embodiments, the gelling agent is selected from the group consisting of xanthan gum, gellan gum, carrageenan, biosaccharide gum-I, sclerotium gum, pectin, pullulan, guar gum, gum arabic, chondroitin, sulfate, alginic acid, sodium hyaluronate, hydrolyzed hyaluronic acid sodium polyglutamate, chitin, chitosan, starch, polyacrylate crosspolymer-6 (SepiMax Zen), and combinations thereof. In some embodiments, the gelling agent is xanthan gum.

In some embodiments, the gelling agent is present in an amount of about 0.1% to about 1% by weight of the TPM liposomal composition. In some embodiments, the gelling agent is present in an amount of about 0.2% by weight of the TPM liposomal composition. In some embodiments, the gelling agent is present in an amount of about 0.3% by weight of the TPM liposomal composition.

In preferred embodiments, a TPM liposomal composition comprises: a liposome, made of a mixture of tocopherol phosphate derivatives, having a lipid bilayer and an internal compartment, a polar solvent system containing pentylene glycol, dimethyl isosorbide, and ethanol, tromethamine or sodium hydroxide as a neutralizing base, and a water soluble phase, wherein one or more lipophilic ingredients is entrapped in the lipid bilayer of the liposome, and one or more water soluble ingredients is dissolved in the water soluble phase in the internal compartment of the liposome, and wherein the TPM liposomal composition has a pH of about 4.5 to about 5.

In preferred embodiments, a TPM liposomal composition comprises: a liposome, made of a mixture of tocopherol phosphate derivatives, having a lipid bilayer and an internal compartment, a polar solvent system containing about 6% pentylene glycol, about 3% dimethyl isosorbide, and about 7% ethanol, about 0.2% sodium hydroxide (a 25% solution) as a neutralizing base, and a water soluble phase, wherein one or more lipophilic ingredients is entrapped in the lipid bilayer of the liposome, and one or more water soluble ingredients is dissolved in the water soluble phase in the internal compartment of the liposome, and wherein the TPM liposomal composition has a pH of about 4.5 to about 5.

In preferred embodiments, a TPM liposomal composition comprises: a liposome, made of a mixture of tocopherol phosphate derivatives, having a lipid bilayer and an internal compartment, a polar solvent system containing about 7% pentylene glycol, about 3.08% dimethyl isosorbide, and about 8% ethanol, about 0.3% tromethamine as a neutralizing base, and a water soluble phase, wherein one or more lipophilic ingredients is entrapped in the lipid bilayer of the liposome, and one or more water soluble ingredients is dissolved in the water soluble phase in the internal compartment of the liposome, and wherein the TPM liposomal composition has a pH of about 4.5 to about 5.

Topical Final Formulation

Embodiments disclosed herein are directed to a topical final formulation comprising: a TPM liposomal composition as described herein, an additive, a solvent, and a cosmetically acceptable excipient, wherein the TPM liposomal composition is present in an amount of about 0.1% to about 40% by weight of the topical final formulation. In certain embodiments, the TPM liposomal composition described herein is part of a topical final formulation at about 1% to about 30%. In certain embodiments, the TPM liposomal composition described herein is part of a topical final formulation at about 20%. In certain embodiments, the TPM liposomal composition described herein is part of a topical final formulation at about 10%.

In certain embodiments, the topical final formulation is formulated in a form selected from the group consisting of a cream, solution, emulsion, semi-solid, jelly, paste, gel, hydrogel, ointment, lotion, emulsion, foam, mousse, liquid, suspension, or dispersion.

In certain embodiments, the topical final formulation is formulated in a product selected from the group consisting of neck cream, neck lotion, body lotion, body cream, face lotion, face cream, eye lash treatment, hair moisturizer, hair conditioner, cellulite treatment, nail conditioner, gel, emulsion, silicone gel, water gel, oil-in-water emulsion, or water-in-oil emulsion.

In some embodiments, the solvent is selected from the group selected from water/aqua/eau, alcohol denatured, alcohol, ethanol, octylodecanol, isohexadecane and combinations thereof. In some embodiments, the solvent contains more than one solvent is selected from water/aqua/eau, alcohol denatured, alcohol, ethanol, octylodecanol, or isohexadecane. In some embodiments, the solvent is present in an amount of about 35% to about 75% by weight of the topical final formulation. In some embodiments, the solvent is water present in an amount of about 35% to about 75% by weight of the topical final formulation. In some embodiments, the solvent comprises both water and ethanol present in a total amount of about 55% to about 60% by weight of the topical final formulation.

In some embodiments, the cosmetically acceptable excipient is selected from the group consisting of a preservative, an antioxidant, a chelator, a filler, a film former, a fragrance, a pH adjuster, and combinations thereof. In some embodiments, the cosmetically acceptable excipient is selected from the group consisting of hydroxyacetophenone, ethylhexylglycerin, sodium phytate, tromethamine, lactic acid, disodium phosphate, phenoxyethanol, xylose, HDI/trimethylol hexyllactone crosspolymer, lactose, ethylhexylglycerine, disodium EDTA, mineral salts, glucose, caprylyl glycol, silica, hexylene glycol, sodium benzoate, fragrance/parfum, BHT, hydrated silica, silica dimethyl silylate, sodium citrate, citric acid, lactic acid, sodium hydroxide, VP/polycarbamyl polyglycol ester, hydrolyzed sesame protein PG-propyl methylsilanediol, glucose, silica, tocopherol, limonene, linalool, isohexadecane, and combinations thereof. In some embodiments, the cosmetically acceptable excipient contains more than one excipient is selected from hydroxyacetophenone, ethylhexylglycerin, sodium phytate, tromethamine, lactic acid, disodium phosphate, phenoxyethanol, xylose, HDI/trimethylol hexyllactone crosspolymer, lactose, ethylhexylglycerine, disodium EDTA, mineral salts, glucose, caprylyl glycol, silica, hexylene glycol, sodium benzoate, fragrance/parfum, BHT, hydrated silica, silica dimethyl silylate, sodium citrate, citric acid, lactic acid, sodium hydroxide, VP/polycarbamyl polyglycol ester, hydrolyzed sesame protein PG-propyl methylsilanediol, glucose, silica, tocopherol, limonene, linalool, or isohexadecane. In some embodiments, the cosmetically acceptable excipient is present in an amount of about 0.1% to about 5% by weight of the topical final formulation. In some embodiments, the cosmetically acceptable excipient is present in an amount of about 1% to about 2% by weight of the topical final formulation.

In certain embodiments, the additive is present in an amount of about 0.1% to about 20% by weight of the topical final formulation.

In some embodiments, the additive is a cosmetic additive selected from the group consisting of vitamins, cosmetic peptides, oil control agents, sensation modifying agents, skin lightening agents, hydrating formulations, a compound that absorbs or reflects UV photons, other skin care agents, and combinations thereof.

In some embodiments, the additive is selected from the group consisting of 3-O-ethyl ascorbic acid, niacinamide, retinaldehyde hydroxysomes, retinyl palmitate, hydroxyapatite, whey protein, Pyrus Malus (apple) fruit extract, calcium PCA, magnesium PCA, retinal, sea salt/maris sal/sel marin, glaucine, adenosine, ceramide NP, cholesterol, ceramide NS, ceramide AP, ceramide EOP, ceramide EOS, caprooyl phytosphingosine, caprooyl sphingosine, ascorbyl palmitate, tocopherol, glycoin, hyaluronic acid, hyaluronic acid derivative, and combinations thereof.

In some embodiments, the additive is glaucine, which promotes fat breakdown and reduces the appearance of double chin and improves contours of the neck and chin.

In some embodiments, the additive is a combination of stacked retinoinds, melanosome transfer inhibitor and vitamin C, wherein the stacked retinoids are selected from retinaldehyde hydroxysomes, retinyl palmitate, retinal, or combinations thereof, which targets photodamaged and hyperpigmented skin. In some embodiments, the skin is the skin of the décolletage.

In some embodiments, the vitamin selected as a cosmetic additive is selected from the group consisting of vitamin D, vitamin K, vitamin B (including niacinamide, nicotinic acid, $C_{1-18}$ nicotinic acid esters, and nicotinyl alcohol; B6 compounds, such as pyroxidine; and B5 compounds, such as panthenol, or "pro-B5"), vitamin A (including retinoids such as retinyl propionate, carotenoids, and other compounds), vitamin E (including tocopherol sorbate, tocopherol acetate, other esters of tocopherol), vitamin C (including ascorbyl esters of fatty acids, and ascorbic acid derivatives, for example, ascorbyl glucoside, magnesium ascorbyl phosphate, sodium ascorbyl phosphate, and ascorbyl sorbate), and all natural and/or synthetic analogs thereof, and combinations thereof. In various embodiments, the topical final formulations may comprise about 0.0001 wt. % to about 20 wt. %, about 0.001 wt. % to about 10 wt. %, about 0.01 wt. % to about 5 wt. %, or about 0.1 wt. % to about 1 wt. %, or any individual concentration or range of each vitamin contained in the topical final formulation.

In some embodiments, the additive is selected from cosmetic peptides selected from the group consisting of di-, tri-, tetra-, penta-, and hexa-peptides, their salts, isomers, derivatives, and mixtures thereof. Examples of useful peptide derivatives include, but are not limited to, peptides derived from soy proteins, palmitoyl-lysine-threonine (pal-KT), palmitoyl-lysine-threonine-threonine-lysine-serine (MATRIXYL®), palmitoyl-glycine-glutamine-proline-arginine (RIGIN®), acetyl dipeptide-1 cetyl ester (IDEA-LIFT™), and Cu-histidine-glycine-glycine (Cu-HGG, also known as IAMIN®), and naturally occurring and synthesized derivatives thereof, and combinations thereof. Some of the peptides are available from Sederma, France. In various embodiments, the topical final formulations may comprise about $1\times10^{-7}$ wt. % to about 20 wt. %, about $1\times10^{-6}$ wt. % to about 10 wt. %, and about $1\times10^{-5}$ wt. % to about 5 wt. %, or any individual concentration or range of each peptide contained in the topical final formulation.

In some embodiments, the additive is selected from oil control agents selected from the group consisting of compounds useful for regulating the production of skin oil, or sebum, and for improving the appearance of oily skin. Examples of oil control agents include, for example, salicylic acid, dehydroacetic acid, benzoyl peroxide, vitamin B3 (for example, niacinamide), and the like, their isomers, esters, salts and derivatives, and mixtures thereof. The topical final formulation of such embodiments may comprise about 0.0001 wt. % to about 15 wt. %, about 0.01 wt. % to about 10 wt. %, about 0.1 wt. % to about 5 wt. %, and about 0.2 wt. % to about 2 wt. %, or any individual concentration or range of each oil control agent contained in the topical final formulation.

In some embodiments, the additive is selected from other skin care agents selected from the group consisting of retinol, steroids, salicylate, minocycline, antifungals, peptides, antibodies, lidocaine, and the like and combinations thereof. In some embodiments, other skin care agents include N-acyl amino acid compounds comprising, for example, N-acyl phenylalanine, N-acyl tyrosine, and the like, their isomers, comprising their D and L isomers, salts, derivatives, and mixtures thereof. An example of a suitable N-acyl amino acid is N-undecylenoyl-L-phenylalanine is commercially available under the tradename SEPIWHITE®. Other skin active agents include, but are not limited to, Lavandox, Thallasine 2, Argireline NP, Gatuline In-Tense and Gatuline Expression, Myoxinol LS 9736, Syn-ake, and Instensyl®, Sesaflash™, N-acetyl D-glucosamine, panthenol (for example, DL panthenol available from Alps Pharmaceutical Inc.), tocopheryl nicotinate, benzoyl peroxide, 3-hydroxy benzoic acid, flavonoids (for example, flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (for example, retinyl propionate), phytic acid, N-acetyl-L-cysteine, lipoic acid, tocopherol and its esters (for example, tocopheryl acetate: DL-a-tocopheryl acetate available from Eisai), azelaic acid, arachidonic acid, tetracycline, ibuprofen, naproxen, ketoprofen, hydrocortisone, acetominophen, resorcinol, hexylresorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof. Further skin care agents are disclosed in US Publication No. 2007/0020220A1, wherein the components/ingredients are incorporated herein by reference in their entirety.

In some embodiments, the additive is a cellulite treatment agent. In some embodiments, the cellulite treatment agent is selected from the group consisting of apigenin, extracts containing Berberine or salts thereof, a blend of pterostilbene (resveratrol dimethyl ether) and xymenynic acid dissolved in glyceryl linoleate and glyceryl linolenate, and combinations thereof.

In some embodiments, the additive is a skin lightening agent or an antiaging ingredient selected from the group consisting of ascorbic acid compounds, vitamin B3 compounds, azelaic acid, butyl hydroxyanisole, gallic acid and its derivatives, glycyrrhizinic acid, hydroquinone, kojic acid, arbutin, mulberry extract, and combinations thereof. In some embodiments, the topical final formulation may comprise Ovaliss ((S)-5,6,6a,7-Tetrahydro-1,2,9,10-tetramethoxy-6-methyl-4H-dibenzo[de,g]quinoline, 1,2-Octanediol, D-Glucopyranose, oligomeric, C10-16-alkyl glycosides, water, ethyl alcohol, and glycerin), Whey protein, MPC (Milk protein complex), Sesaflash (Glycerin, Acrylates copolymer, PVP/polycarbamyl polyglycol ester, Hydrolyzed Sesame Protein PG—propyl methylsilanediol), Majestem (glycerin, Leontopodium Alpinum Callus Culture Extract and xanthan gum), Idealift (butylene glycol, sorbitan laurate, hydroxyethylcellulose, and acetyl dipeptide-1 cetyl ester), and combinations thereof.

In some embodiments, the topical final formulation may further comprise an emollient or lubricating vehicle that help hydrate the skin can also be used. In some embodiments, the emollient is selected from the group consisting of dimethicone, isononyl isononanoate, cetyl ethylhexanoate, Jojoba Esters, cyclopentasiloxane, Helianthus Annuus (Sunflower) Seed Wax, Helianthus Annuus (Sunflower) Seed oil, caprylic/capric triglyceride, Acacia Decurrens Flower Wax, Polyglycerin-3, glycerin, diglycerin, Butyrospermum Parkii (Shea) Butter, petrolatum, petrolatum plus volatile silicones, lanolin, cold cream (USP), hydrophilic ointment (USP), and combinations thereof. In some embodiments, the emollient is present in an amount of about 2% to about 20% by weight of the topical final formulation. In some embodiments, the emollient is present in an amount of about 12% to about 18% by weight of the topical final formulation.

In some embodiments, the topical final formulation may further comprise an elastomer selected from the group consisting of dimethicone/vinyl dimethicone crosspolymer, polysilicone-11, and combinations thereof. In some embodiments, the elastomer is present in an amount of about 0.1% to about 1% by weight of the topical final formulation. In some embodiments, the elastomer is present in an amount of about 0.2% to about 0.4% by weight of the topical final formulation.

In some embodiments, the topical final formulation may further comprise an emulsifier or surfactant selected from the group consisting of octyldodecanol, octyldodecyl xyloside, PEG-30, dipolyhydroxystearate, polysorbate 80, sorbitan oleate, C14-22 alcohols, C12-20 alkyl glucoside, cetearyl alcohol, cetearyl glucoside, glyceryl glucoside, potassium cetyl phosphate, bis-PEG-12 demethicone, lecithin, decyl glucoside, ceteareth-25, cetyl alcohol, behenic acid, coco-glucoside, and combinations thereof. In some embodiments, the emulsifier is present in an amount of about 0.5% to about 10% by weight of the topical final formulation. In some embodiments, the emulsifier is present in an amount of about 3% to about 7% by weight of the topical final formulation.

In some embodiments, the topical final formulation may further comprise a gelling agent selected from the group consisting of acrylamide/sodium acrylpyldimethyl taurate copolymer, sodium acrylpyldimethyl taurate, sodium acrylates copolymer, sodium polyacrylate, carbomer, cetyl hydroxyethylcellulose, gellan gum, and combinations thereof. In some embodiments, the gelling agent is present in an amount of about 0.1% to about 5% by weight of the topical final formulation. In some embodiments, the gelling agent is present in an amount of about 0.2% to about 0.6% by weight of the topical final formulation.

In some embodiments, the topical final formulation may further comprise a humectant selected from the group consisting of glycerin, diglycerin, sodium acetylated hyaluronate, pentylene glycol, hexylene glycol, sodium hyaluronate, and combinations thereof. In some embodiments, the humectant is present in an amount of about 2% to about 10% by weight of the topical final formulation. In some embodiments, the humectant is present in an amount of about 4% to about 7% by weight of the topical final formulation.

In some embodiments, the topical final formulation may further comprise a sensation modifying agent selected from the group of a cooling agent, a warming agent, a relaxing or soothing agent, a stimulating or refreshing agent, and combinations thereof.

In some embodiments, the topical final formulation may further comprise a cooling agent is selected from but not limited to menthol; an isomer of menthol, a menthol derivative; 4-Methyl-3-(1-pyrrolidinyl)-2[5H]-furanone; WS-23, Icilin, Icilin Unilever Analog, 5-methyl-4-(1-pyrrolidinyl)-3-[2H]-furanone; 4,5-dimethyl-3-(1-pyrrolidinyl)-2[5H]-furanone; isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxas-piro[4,5]decane-2-methanol, menthyl succinate and its alkaline earth metal salts, trimethylcyclohexanol, N-ethyl-2-isopropyl-5-methylcyclohexanecarb-oxamide, Japanese mint (Mentha arvensis) oil, peppermint oil, menthone, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide and spearmint oil.

In some embodiments, the topical final formulation may further comprise a warming agent is selected from but not limited to polyhydric alcohols, capsaicin, capsicum powder, a capsicum tincture, capsicum extract, capsaicin, hamamalis, homocapsaicin, homodihydrocapsaicin, nonanoyl vanillyl amide, nonanoic acid vanillyl ether, vanillyl alcohol alkyl ether derivatives, such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol and gingeron.

In some embodiments, the topical final formulation may further comprise a relaxing or soothing agent is selected from but not limited to herb extracts, selected from the group consisting of aloe vera, alpha bisabolol, D-panthenol, allantoin, hamamelis, chamomile, yarrow; calendula, comfrey, witch hazel and other astringents, sea weed, and oat extracts; oils, selected from the group consisting of: almond oil, avocado oil, and comfrey; and essential oils, selected from the group consisting of: cardamone, eucalyptus, Mentha piperita (peppermint), hyssop, and rosemary; waxy or unctuous substances selected from the group consisting of: lanolin or petroleum jelly, minerals, selected from the group consisting of: zinc oxide, calamine and selenium; vitamins, selected from the group consisting of: tocopheryl acetate (vitamin E).

In some embodiments, the topical final formulation may further comprise a stimulating or refreshing agent is selected from but not limited to an alcohol, L-menthol, camphor, menthe oil, capsicum extract, capsaicin, benzyl nicotinate, salicylate, glycol salicylate, acetyl choline, serotonin, histamine, a prostaglandin, a neurotransmitter; a CNS stimulant, caffeine and quinine.

In some embodiments, the topical final formulation has a pH of about 5 to about 7.

In some embodiments, the topical final formulation described herein may be formulated as a liquid. Liquid dosage forms for topical administration may comprise diluents such as, for example, alcohols, glycols, oils, water, and the like. Such compositions may also include wetting agents.

In some embodiments, the topical final formulation described herein may be formulated into an oil-in-water or water-in-oil emulsion. A cream can be a water-in-oil (w/o) emulsion in which an aqueous phase is dispersed in an oil phase, or an oil-in-water (o/w) emulsion in which an oil is dispersed within an aqueous base. An ointment generally refers to a more viscous oil-in-water cream. Traditional ointment bases (i.e. carrier) include hydrocarbons (petrolatum, beeswax, etc.) vegetable oils, fatty alcohols (cholesterol, lanolin, wool alcohol, stearyl alcohol, etc.) or silicones. Insoluble solids such as starch, zinc oxide, calcium carbonate, or talc can also be used in ointments and creams. Gel forms of the compositions described above can be formed by the entrapment of large amounts of aqueous or aqueous-alcoholic liquids in a network of polymers or of colloidal solid particles. Such polymers or colloids (gelling or thickening agents) are typically present at concentrations of less than 10% w/w and include carboxymethyl cellulose, hydroxypropylmethyl cellulose, hydroxyethyl cellulose, methyl cellulose, sodium alginate, alginic acid, pectin, tragacanth, carrageen, agar, clays, aluminum silicate, carbomers, and the like.

In some embodiments, the topical final formulation described herein may be formulated as aerosols, in which the composition is dissolved in a propellant such as dichlorodifluoromethane, trichlorofluoromethane, dichlorotetrafluoroethane, carbon dioxide, or other suitable gas, and a co-solvent such ethanol, acetone, hexadecyl alcohol, and the like and combinations thereof.

In some embodiments, the topical final formulation described herein may be in the form of hydrogels. Hydrogels are typically prepared by cross-linking various monomers and/or polymers to provide a three-dimensional polymer network. Non-limiting examples of polymers include, polyoxyethylene-polypropylene block copolymers, ionic poly saccharides, such as chitosan or sodium alginate, cellulose, and biodegradable polymers, such as poly-lactides (PLA) and poly-glycolides (PGA), butylene succinate (PBS), polyhydroxyalkanoate (PHA), polycaprolactone acid lactone (PCL), polyhydroxybutyrate (PHB), glycolic amyl (PHV), PHB and PHV copolymer (PHBV), and poly lactic acid (PLA)-polyethylene glycol (PEG) copolymers (PLEG).

In some embodiments, the topical final formulation described herein may be coated on bandages, mixed with bio adhesives, or included in dressings.

In some embodiments, the topical final formulation described herein may be used in combination with a cosmetic device.

In some embodiments, the topical final formulation described herein may be used in combination with a patch.

In some embodiments, the topical final formulation described herein is part of an anti-aging regimen.

Methods of Using Compositions Described Herein

Embodiments are directed to methods of improving the look of skin in a human subject in need thereof comprising topically administering to the skin of the subject a topical final formulation as described herein.

In some embodiments, improving the look of skin is an improvement in a characteristic of the skin. In some embodiments, the characteristic of the skin is selected from the group consisting of firmness, elasticity, fine lines and wrinkles, skin texture, skin tone, and any combination thereof. In some embodiments, improving the look of the skin results in smoother, firmer, younger-looking skin. In some embodiments, improving the look of the skin results in a brighter complexion, improved texture, and even-looking skin. In some embodiments, the skin is the neck or décolletage skin of the subject.

Embodiments are directed to methods of improving the look of skin of the neck and décolletage in a subject in need thereof comprising topically administering to the skin of the subject a topical final formulation as described herein.

Embodiments are directed to methods of improving a keloid scar in a subject in need thereof comprising topically administering to the skin of the subject a topical final formulation as described herein.

Embodiments are directed to methods of improving the appearance of aged skin in a subject in need thereof comprising topically administering to the skin of the subject a topical final formulation as described herein. In some embodiments, improving the appearance of aged akin includes improvement of sagging or crepey skin on the face, body or neck. In some embodiments, improving the appearance of aged skin results in smoother, firmer, younger-looking skin.

Embodiments are directed to methods of improving the appearance of various keratinous fibers in a subject in need thereof comprising topically administering to the skin of the subject a topical final formulation as described herein.

In some embodiments, improving aging skin is an improvement in a characteristic of the skin. In some embodiments, the characteristic of the skin is selected from the group consisting of firmness, elasticity, fine lines and wrinkles, skin texture, skin tone, and any combination thereof. In some embodiments, improving the look of the skin results in smoother, firmer, younger-looking skin. In some embodiments, improving the look of the skin results in a brighter complexion, improved texture, and even-looking skin. In some embodiments, the skin is the neck or décolletage skin of the subject.

Embodiments are directed to methods of improving the contour of the neck or jawline in skin of a subject in need thereof comprising topically administering to the skin of the subject a topical final formulation as described herein.

Embodiments are directed to methods of decreasing the appearance of cellulite in skin of a subject in need thereof comprising topically administering to the skin of the subject a topical final formulation as described herein.

Embodiments are directed to methods of increasing expression of an extracellular matrix protein in skin of a subject in need thereof comprising topically administering to the skin of the subject a topical final formulation as described herein.

Embodiments are directed to methods of increasing expression of an extracellular matrix protein in a model system based on a cell-based assay using adult human dermal fibroblasts, or in a 3-dimensional reconstructed skin model comprising administering a TPM liposomal composition as described herein.

In some embodiments, the extracellular matrix protein is selected from, but not limited to, the group consisting of decorin, type I collagen, type III collagen, elastin, hyaluronate, and combinations thereof.

In some embodiments, the TPM liposomal composition or topical final formulation used for increasing expression of decorin is at a concentration of about 5 µg/mL to about 50 µg/mL. In some embodiments, the increased expression or upregulation is in a percentage of about 130% to about 200%. In some embodiments, the percentage of increased expression or upregulation is statistically significant. Without wishing to be bound by theory, decorin is a small cellular or pericellular matrix proteoglycan protein is a component of connective tissue, binds to type I collagen fibrils, and plays a role in matrix assembly. Decorin is an important component of the extracellular matrix. Decorin is a component of connective tissue, binds to type I collagen fibrils, and plays a role in matrix assembly. Decorin appears to influence fibrillogenesis, and also interacts with fibronectin, thrombospondin, the complement component C1q, epidermal growth factor receptor (EGFR) and transforming growth factor-beta (TGF-beta). Keloid scars have decreased decorin expression compared to healthy skin. The primary function of decorin involves regulation during the cell cycle. It has been involved in the regulation of autophagy, of endothelial cell and inhibits angiogenesis. Decorin, the main proteoglycan in skin, has a small size with a core protein of approximately 40 kDa and one chondroitin sulfate/dermatan sulfate glycosaminoglycan (GAG) chain. The main function of decorin is to regulate the collagen matrix assembly. Decorin is distributed along collagen fibrils with the core protein and the decorin GAG chain controls the distance between the collagen fibrils. Reducing the length of the decorin GAG chain reduces the distance between the collagen fibrils. Age-related changes in decorin are apparent in the GAG chain in respect to the molecular size and sulfate position but not in the core protein. Structural changes in the decorin GAG chain may be involved in changes in collagen matrix assembly during the aging process.

In some embodiments, the TPM liposomal composition or topical final formulation used for increasing expression of collagens is at a concentration of about 5 µg/mL to about 500 µg/mL. In some embodiments, the increased expression or upregulation is in a percentage of about 110% to about 130%. In some embodiments, collagen may be selected from collagen type I, collagen type II, collagen type III, collagen type IV, or collagen type V and combinations thereof. In some embodiments, the collagen can be fibrillary collagen or non-fibrillary collagen and combinations thereof. Low molecular weight collagens can be made, for example, by hydrolysis.

In some embodiments, the TPM liposomal composition or topical final formulation used for increasing expression of elastin is at a concentration of about 5 µg/mL. In some embodiments, the increased expression or upregulation is in a percentage of about 130%. In some embodiments, the percentage of the increased expression or upregulation is statistically significant. Without wishing to be bound by theory, elastin is a protein found in connective tissue and allows many tissues in the body to resume their shape after stretching or contracting.

In some embodiments, the TPM liposomal composition or topical final formulation used for increasing expression of hyaluronate is at a concentration of about 5 μg/mL. In some embodiments, the increased expression or upregulation is in a percentage of about 150%. In some embodiments, the percentage of the increased expression or upregulation is statistically significant. Without wishing to be bound by theory, hyaluronate, is a salt or ester of hyaluronic acid, and is known to interact with CD44, a receptor for hyaluronic acid-mediated motility (RHAMM), and intercellular adhesion molecule-1 (ICAM-1). CD44 is widely distributed throughout the body and mediates cell interaction with hyaluronic acid. ICAM-1 is a metabolic cell surface receptor for hyaluronic acid, and binding of hyaluronic acid to ICAM-1 may contribute to the control of ICAM-1-mediated inflammatory activation.

In some embodiments, the topical final formulation can be applied to the skin one, two, three, four, five or more times each day, and application can be carried out for a period of at least 1 month, 2 months, 3 months, 4 months, 6 months, 8 months or 12 months.

In some embodiments, the topical final formulation may be administered once, as needed, once daily, twice daily, three times a day, once a week, twice a week, every other week, every other day, or the like for one or more dosing cycles. A dosing cycle may comprise administration for about 1 week, about 2 weeks, about 3 weeks, about 4 weeks, about 5 weeks, about 6 weeks, about 7 weeks, about 8 weeks, about 9 weeks, or about 10 weeks. After this cycle, a subsequent cycle may begin approximately 1, 2, 3, 4, 5, 6, 7, 8, 9, 10, 11, or 12 weeks later. The treatment regime may comprise 1, 2, 3, 4, 5, or 6 cycles, each cycle being spaced apart by approximately 1, 2, 3, 4, 5, 6, 7, 8, 9, 10, 11, or 12 weeks.

In some embodiments, the methods may comprise a variety of additional steps including, for example, cleaning the surface tissue at the site of applying, abrading, microdermabrasion, toning, and the like.

Methods of Preparing Compositions Described Herein

Broadly speaking, the compositions may be prepared by combining together the components of the formulation, as described herein, at a temperature and for a time sufficient to provide a topically acceptable composition.

Embodiments are directed to methods for preparing a TPM liposomal composition comprising:
a) mixing a lipophilic ingredient with a polar solvent system (such as dimethyl isosorbide (DMI) and pentylene glycol) and heating the resulting mixture to a temperature between about 60° C. to about 65° C.;
b) adding a tocopherol phosphate derivative ingredient to the mixture from step a) once temperature reaches about 57.9° C. to about 61° C., heating and maintaining the temperature of the resulting mixture to between about 57.9° C. to about 61° C. until all contents melted;
c) cooling the mixture from step b) to a temperature between about 32° C. to about 35° C., adding one or more lipophilic ingredients and ethanol into the cooled mixture, and mixing the mixture until complete dissolution to form Phase A;
d) mixing, in a separate container, one or more water soluble ingredients, and water thoroughly and keeping the resulting mixture at a temperature between about 38° C. to about 40° C. to form Phase B;
e) adding Phase A into Phase B and mixing the resulting mixture at a temperature between about 38° C. to about 40° C. for at least 20 minutes;
f) adding a neutralizing base such as tromethamine;
g) dispersing a gelling agent, such as xanthan gum, into a humectant, such as glycerin, to form Phase C and missing into solution of step e); and
h) turning off the heat to the mixture of step g) and stirring the mixture until the temperature of the mixture reaches room temperature.

In some embodiments, the method requires that a base is added at step e).

In some embodiments, one or more ingredient is temperature sensitive.

In some embodiments, the mixing at step e) is continuous for about 18 to about 22 minutes. In some embodiments, the mixing at step e) is continuous for about 20 minutes.

In some embodiments, the temperature at step a) is about 60° C. to about 65° C. In some embodiments, the temperature at step b) is about 57.9° C. to about 61° C. In some embodiments, the temperature at step c) is about 32° C. to about 35° C. In some embodiments, the temperature at step d) is about 38° C. to about 40° C. In some embodiments, temperature at step e) is about 38° C. to about 40° C. In certain embodiments, the TPM liposomal composition is added to a final formulation at about 0.1% to about 40% by weight of the topical final formulation, wherein the final formulation additionally includes an additive, water, and a cosmetically acceptable excipient. In certain embodiments, the final formulation is selected from the group consisting of neck cream, neck lotion, body lotion, body cream, face lotion, face cream, eye lash treatment, hair moisturizer, hair conditioner, cellulite treatment, nail conditioner, gel, emulsion, silicone gel, water gel, oil-in-water emulsion, or water-in-oil emulsion.

Product By Process

In embodiments described herein a tocopherol phosphate mixture (TPM) liposomal composition is formed by a method comprising the steps of:
a) mixing, in a first container, a lipophilic ingredient with a polar solvent system and heating the resulting mixture to a temperature of at least about 60° C.,
b) adding a tocopherol phosphate derivative ingredient to the mixture from step a) and maintaining a temperature sufficient to melt all contents,
c) cooling the mixture from step b) to a temperature of from about 32° C. to about 35° C., and, once cooled, adding one or more lipophilic ingredients and ethanol into the cooled mixture, with mixing until complete dissolution, to form a Phase A,
d) mixing, in a second container, one or more water soluble ingredients and water at a temperature between about 38° C. to about 40° C. to form a Phase B;
e) adding Phase A into Phase B and mixing at a temperature between about 38° C. to about 40° C. for at least 20 minutes;
f) adding a neutralizing base,
g) dispersing xanthan gum into glycerin to form Phase C and mixing into solution of step e), and
h) cooling the mixture of step g), while stirring, to room temperature.

In certain embodiments, the polar solvent system of step a) comprises a mixture of dimethyl isosorbide (DMI) and pentylene glycol.

In certain embodiments, the temperature in step b) is maintained at from about 57.9° C. to about 61° C.

In certain embodiments, the neutralizing base comprises tromethamine.

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1: Compositions Ex. 1-Ex. 9

Compositions Ex. 1 and Ex. 2 were prepared with various water soluble actives which proceeded without incident into the liposome formation. Composition Ex. 1 can be made using Process 1 and Process 2, as described in Example 4 below.

Composition Ex. 1 has 2.7% TPM, 8% Ethanol, 2.5% of a combination of three water soluble actives, and two lipophilic soluble ingredients. In addition, Composition Ex. 1 has a ratio of ethanol:PG:DMI of 2.59:2.27:1. Composition Ex. 2 has slightly less TPM (2.5%) only a single water soluble active, and ethanol:PG:DMI ratio of 1.71:1.47:1 and three oil soluble ingredients in the liposome phase. Surprisingly, increasing the level of dipalmitoyl hydroxyproline in Ex. 2, to more than 1.0%, resulted in the formation of a precipitate as observed by optical microscopy (see Table 3) using Process 2. Suggesting a specific range of dipalmitoyl hydroxyproline that can be used to form Ex. 1 and Ex. 2. The formation of the precipitate should be avoided as it may change the aesthetics, performance, efficacy and usage of the final product.

TABLE 1

| | | | Compositions Ex. 1-Ex. 4. | | | |
|---|---|---|---|---|---|---|
| Phase | role | INCI | Ex. 1 | Ex. 2 | Ex. 3 | Ex. 4 |
| B | solvent | AQUA | 73.1 | 75.8 | 75.3 | 74.3 |
| | water soluble amino acid or vitamin | Arginine or Niacinamide (and/or) 3-O-Ethyl Ascorbic Acid | 2.5 | 0.5 | 0.5 | 0.5 |
| A | polar solvent | DIMETHYL ISOSORBIDE (DMI) and PENTYLENE GLYCOL (PG) | 10.08 | 10.08 | 10.08 | 10.08 |
| | Vitamin E/ tocopherol phosphate derivative | ALPHA-TOCOPHERYL PHOSPHATE AND DI-ALPHA-TOCOPHERYL PHOSPHATE (TPM) | 2.7 | 2.5 | 2.5 | 2.5 |
| | Hydrophobic ingredient | DIPALMITOYL HYDROXYPROLINE | 1.0 | 1.0 | 1.5 | 2.5 |
| | | retinoid (and/or) 3-O-CETYL ASCORBIC ACID | 0.12 | 0.62 | 0.62 | 0.62 |
| | alcohol | ALCOHOL DENAT. (ethanol) | 8.0 | 7.0 | 7.0 | 7.0 |
| C | base | TROMETHAMINE | 0.3 | 0.2 | 0.2 | 0.2 |
| | water phase gelling agent | XANTHAN GUM | 0.2 | 0.3 | 0.3 | 0.3 |
| | humectant | GLYCERIN | 2.0 | 2.0 | 2.0 | 2.0 |
| | Solvent ratio | Ethanol:Pentylene Glycol:DMI ratio | 2.59:2.27:1 | 1.71:1.47:1 | 1.71:1.47:1 | 1.71:1.47:1 |

Impact of solvents and process on the formation of liposomes. Investigation of the importance of solvent mixture and process in the preparation of the desired liposome technology (Ex. 1 and Ex. 2) revealed that formation of the liposomes, containing ingredients listed in Ex. 1 and Ex 2, were most successful using the optimized solvent system of Ethanol:Pentylene Glycol:DMI (from a ratio of 1.71:1.47:1 to 2.59:2.27:1) and Processes 1 and 2. Preparation of Ex. 2 (which is also the same composition of Ex. 6-8 just formed using a different process) following Processes 3-6 was not successful as it resulted in the formulation of a precipitate (see Table 4) which may be an undesirable result, as this may impact the end product performance, aesthetics, appearance and quality. Ex. 5 was performed using Process 3 in the absence of ethanol and this resulted in precipitate. Addition of ethanol after formation of the liposome did not resolve precipitate issue (Process 4, Ex. 6, Table 2 and 4), nor did adding energy by homogenization (Process 5 and 6, Ex. 7 and 8, Table 2 and 4).

TABLE 2

Impact of solvents and processes on the formation of liposomes, Compositions Ex. 5-Ex. 9.

| Phase | role | INCI | Ex. 5 | Ex. 6 | Ex. 7 | Ex. 8 | Ex. 9 |
|---|---|---|---|---|---|---|---|
| B | solvent | Aqua/water | 82.8 | 75.8 | 75.8 | 75.8 | 77 |
|  | water soluble amino acid or vitamin | Arginine or Niacinamide (and/or) 3-O-Ethyl Ascorbic Acid | 0.5 | 0.5 | 0.5 | 0.5 | 0.5 |
| A | polar solvent | Dimethyl isosorbide (and) pentylene glycol | 10.08 | 10.08 | 10.08 | 10.08 | 9 |
|  | Vitamin E/ tocopherol phosphate derivative | ALPHA-TOCOPHERYL PHOSPHATE AND DI-ALPHA-TOCOPHERYL PHOSPHATE (TPM) | 2.5 | 2.5 | 2.5 | 2.5 | 2.5 |
|  | Hydrophobic ingredient | retinoid (and/or) 3-O-CETYL ASCORBIC ACID | 0.62 | 0.62 | 0.62 | 0.62 | 1.5 |
|  |  | Dipalmitoyl hydroxyproline | 1.0 | 1.0 | 1.0 | 1.0 |  |
|  | alcohol | ALCOHOL DENAT. (ethanol) | 0 | 7.0 | 7.0 | 7.0 | 7 |
| C | base | TROMETHAMINE [Ex. 9 25% Sodium Hydroxide] | 0.2 | 0.2 | 0.2 | 0.2 | 0.2 |
|  | water phase gelling agent | XANTHAN GUM | 0.3 | 0.3 | 0.3 | 0.3 | 0.3 |
|  | humectant | GLYCERIN | 2.0 | 2.0 | 2.0 | 2 | 2 |
|  | Solvent | Ethanol:Pentylene Glycol:DMI ratio | 0:1.47:1 | 1.71:1.47:1 | 1.71:1.47:1 | 1.71:1.47:1 | 2.3:2:1 |
|  |  | Process | 3 | 4 | 5 | 6 | 2 |

Additional characteristics of Compositions Ex. 1-Ex. 8 are presented in Tables 3 (particle size according to Method A and turbidity according to Method B) and 4 (optical microscopy according to Method C), n.d.=not determined.

TABLE 3

Particle size and Turbidity.

| Examples | Process | Particle Size Method A (nm) | Particle Size, polydispersity (Method G) | Turbidity (NTU) |
|---|---|---|---|---|
| 1 | 1 | n.d. | n.d. | 947 |
| 2 | 2 | 537.0 ± 169.1 | 342.7, 0.276 | 4584 |
| 3 | 2 | 659 ± 818 | n.d. | 5466 |
| 4 | 2 | n.d. | n.d. | n.d. |
| 5 | 3 | 554.2 ± 214.2 | n.d. | 5777 |
| 6 | 4 | 517.5 ± 157.5 | n.d. | 3719 |
| 7 | 5 | 387.7 ± 1076 | n.d. | 4399 |
| 8 | 6 | 558.3 ± 213.7 | n.d. | 2927 |

TABLE 4

Optical microscopy of compositions Ex. 1-Ex. 8.
Note that image shown is prior to neutralization
and addition of the gel phase for simplicity.

| Examples | Magnification | Precipitate/no precipitate |
|---|---|---|
| 1 | 40 X | none |
| 2 | 40 X | none |
| 3 | 40 X | yes |
| 4 | 10 X | yes |
| 5 | 10 X | yes |
| 6 | 10 X | yes |
| 7 | 10 X | yes |
| 8 | 10 X | yes |

Method A: Particle size analysis by Lumisizer. Samples diluted in water immediately after completion of the batch or 24 hours later with a dilution 1 part formula to 4 or 5 parts water. Method centrifugation at RPM=4000, 5 cycles, 23° C. Particle size determined using polystyrene as dispersed phase, with an average of 3-4 nodes, distributed evenly.

Method B: Turbidity. Turbidity of samples determined on a Hach TL-23 benchtop turbidity meter.

Method C: Optical microscopy. Small aliquots of material were taken after the addition of the lipophilic phase to the water phase prior to neutralization and observed under a VWR Optical microscope with or without polarization. Samples were evaluated for the presence or absence of precipitate at 10× or 40× magnification.

Method G: Particle Size, polydispersity. 100 μL of each sample was diluted 1000 times with DI water to obtain a clear to slightly hazy solution. Diluted solutions were vortexed using a VWR Mini Vortexer at a speed setting of 9 for 45 seconds to ensure homogeneity before analysis. Particle Size Measurements. A Brookhaven Zetasizer was used to measure the particle size of each sample. Each sample was measured 5 times and the mean diameter was calculated.

Example 2: Effect of Compositions Ex. 1 and Ex. 2 on the Level of ECM Components Compositions Ex. 1 and Ex. 2 successfully formed liposomes without precipitate and were therefore evaluated in a cell-based assay to evaluate their effect on the metabolism, proliferation and output of extracellular matrix (ECM) components in adult human dermal fibroblast culture model (Method E, Table 5). Compositions Ex. 1 and Ex. 2 are comparable in efficacy in terms of their activity in this cell-based model system.

TABLE 5

Effect of Compositions Ex. 1 and Ex. 2 on the level of ECM components corrected for cell numbers (std cell #) and expressed as % of water control.

| Test Material | Type I Collagen (% CTR) | p-value | Type III collagen (% CTR) | p-value | decorin (% CTR) | p-value | elastin (% CTR) | p-value | Hyaluronian (% CTR) | p-value |
|---|---|---|---|---|---|---|---|---|---|---|
| water | 100 | 1.000 | 100 | 1.000 | 100 | 1.000 | 100 | 1.000 | 100 | 1.000 |
| bFGF 10 ng/mL | 67 | 0.005 | 87 | 0.180 | 57 | 0.000 | 62 | 0.000 | 72 | 0.001 |
| Ex. 1 500 μg/ml | 124 | 0.017 | 116 | 0.101 | 93 | 0.505 | 111 | 0.474 | 111 | 0.237 |
| Ex. 1 50 μg/ml | 103 | 0.722 | 115 | 0.045 | 94 | 0.320 | 92 | 0.288 | 89 | 0.153 |
| Ex. 1 5 μg/ml | 86 | 0.057 | 110 | 0.160 | 153 | 0.009 | 128 | 0.027 | 147 | 0.001 |
| Ex. 2 500 μg/ml | N/A | N/A | N/A | N/A | N/A | N/A | N/A | N/A | N/A | N/A |
| Ex. 2 50 μg/ml | 102 | 0.885 | 118 | 0.105 | 83 | 0.038 | *108* | *0.347* | 109 | 0.379 |
| Ex. 2 5 μg/ml | *109* | *0.061* | 139 | 0.077 | 102 | 0.266 | *107* | *0.167* | 96 | 0.841 |

Macromolecules of interest were quantified either in the soluble state (i.e. decorin, type I collagen, type III collagen, and hyaluronate) or insoluble, on fixed cells (i.e. total insoluble proteins and elastin). Data is corrected for cell number according to Equation 1 (see Method E below). Composition Ex. 1 showed a slight increased expression or upregulation of Type I and Type III Collagen with increasing concentration of the formulation from 5 to 500 µg/mL as well as statistically significant upregulation of elastin and hyaluronian at 5 µg/mL. Unexpectedly, Ex. 1 showed a very significant increased expression or upregulation of decorin. In this model, Composition Ex. 2 showed statistically significant increased expression or upregulation of type III collagen at 5 and 50 µg/mL, and a directional increased expression or upregulation of type I collagen and elastin at 5 µg/mL (Table 5, italic). N/A designate experimental conditions where there was a >50% decrease in the cell number compared to water-treated control. Significant results are bold and directional results are in italic.

Method E: Metabolism, Proliferation and Output of ECM Components in the Adult Human Dermal Fibroblast Culture Model. Test materials were dissolved in sterile cell culture medium at ×2 highest concentration tested and samples were added in triplicates to exponentially growing adult human dermal fibroblasts (aHDF; 7,000 cells/well of a 96 well plate; p.7 Cell Applications, San Diego, CA, cat. #106-05a; lot #3014). Cultures were maintained in DMEM/10% FBS. At the end of the experiments (day 7), macromolecules of interest were quantified either in the cell culture medium (decorin, type I collagen, type III collagen and hyaluronate) or on fixed cells (total insoluble proteins and elastin), by ELISA and sulforhodamine B, as indicated in Tables II-IV. Total insoluble (cytoskeletal) proteins were quantified to determine the effect of test materials on cell proliferation (cell numbers or cell #) according to the method described by Voigt et al., 2005. These values were also used to standardize decorin, type I collagen, type III collagen, elastin and hyaluronate output data to cell numbers, using the Equation 1:

(Standardized Cell #)=[macromolecule of interest raw read out value]/cell number raw read out value]  Equation 1

This standardization was performed separately for each well. Each experimental condition and control was assayed at least in triplicates. The effect of test materials on mitochondrial metabolism was measured with the MTT assay, which measures the activity of mitochondrial dehydrogenases, such as succinate dehydrogenase, implicated in the respiratory electron transport chain in mitochondria (Berridge & Tan; 1993). The positive control for cell proliferation and metabolic activity was basic fibroblast growth factor (bFGF). All colorimetric measurements were performed using Molecular Devices microplate reader MAX190 and SoftMax3.1.2PRO software. Statistical significance was assessed with paired Student test. Deviations of ≥20% as compared to water control with p values below 0.05 were considered statistically significant.

Example 3: The Effect of Compositions Ex. 1 and Ex. 2 on the Level of Soluble and Insoluble Decorin Compositions Ex. 1 and Ex. 2 were tested to further confirm the results for the increased expression or upregulation of decorin. Results presented in Table 4. It was confirmed that both Compositions Ex. 1 and Ex. 2 were shown to unexpectedly upregulate soluble and insoluble Decorin (see Table 6). Composition Ex. 1 upregulated soluble decorin at low concentrations from 5 to 50 µg/mL and Composition Ex. 2 at higher concentrations at 50 µg/mL. In addition, Composition Ex. 1 upregulated insoluble decorin at both 5 and 50 µg/mL with 50 µg/mL showing the most statistically significant result under these conditions. Composition Ex. 2 shows a comparable pattern of statistically significant upregulation of insoluble decorin at 50 µg/mL and directional upregulation at 5 µg/mL. Without being bound to any particular theory, the activity observed is not related to the alpha-tocopheryl phosphate and di-alpha-tocopheryl phosphate (TPM) as this compound tested on its own did not show activity in this assay (see Table 6, test sample Ref. 1). Ref. 1 is a commercially available pre-neutralized mixture of TPM, containing disodium lauriminodipropionate tocopheryl phosphate. N/A are experimental conditions where there was a >50% decrease in the cell number compared to water-treated control. Statistically significant results in bold, directional results are italicized. Results collected according to Method F, see below.

TABLE 6

The effect of test samples of the level of soluble and insoluble decorin standardized to cell numbers (std cell#) and expressed as a % of water control.

| Ex. | Concentration | Soluble decorin (% CTR) | p-value | Insoluble decorin % CTR) | p-value |
|---|---|---|---|---|---|
| water | water | 100 | 1.000 | 100 | 1.000 |
| bFGF | 10 ng/mL | 67 | 0.005 | 87 | 0.180 |
| Ref. 1 | 1 mg/mL | N/A | N/A | N/A | N/A |
| Ref. 1 | 100 µg/mL | N/A | N/A | N/A | N/A |
| Ref. 1 | 10 µg/ml | 84 | 0.296 | 100 | 0.985 |
| Ref. 1 | 1 µg/mL | 73 | 0.078 | 81 | 0.264 |
| Ex. 1 | 500 µg/ml | N/A | N/A | N/A | N/A |
| Ex. 1 | 50 µg/ml | 131 | 0.053 | 188 | 0.000 |
| Ex. 1 | 5 µg/ml | 147 | 0.009 | 117 | 0.310 |
| Ex. 2 | 500 µg/ml | N/A | N/A | N/A | N/A |
| Ex. 2 | 50 µg/ml | 141 | 0.011 | 197 | 0.000 |
| Ex. 2 | *5 µg/ml* | *112* | *0.442* | *127* | *0.158* |

The upregulation of decorin in conjunction with the decreased fibroblast proliferation by Compositions Ex. 1 and Ex. 2 demonstrated that these compositions can be used for treating keloid scars. Further, insoluble decorin is the one deposited and incorporated in the ECM. The soluble fraction may be the combination of newly synthetized protein and proteolyzed fragments.

Method F: Test materials were dissolved in sterile cell culture medium at ×2 highest concentration tested and samples were added in triplicates to exponentially growing adult human dermal fibroblasts (7,000 cells/well of a 96 well plate; p.7 Cell Applications, San Diego, CA, cat. #106-05a; lot #3014). Cultures were maintained in DMEM/10%FBS. At the end of the experiment (day 7), decorin was quantified in the cell culture medium (soluble fraction) and on fixed cells (insoluble fraction) by ELISA. Total insoluble (cytoskeletal) proteins were quantified to determine the effect of test materials on cell proliferation (cell numbers or cell #) according to the method described by Voigt et al., 2005. These values were also used to standardize decorin output data to cell numbers, using Equation 1. This standardization was performed separately for each well. Each experimental condition and control was assayed at least in triplicates. The effect of test materials on mitochondrial metabolism was measured with the MTT assay, which measures the activity of mitochondrial dehydrogenases, such as succinate dehydrogenase, implicated in the respiratory electron transport chain in mitochondria (Berridge & Tan; 1993).

Example 4: Processes for Preparations of Compositions

Process 1:
1. In a side kettle on a hot plate heat DMI, pentylene glycol, and hydrophobic amino acid to 60-65° C. with stir bar. Cover beaker with foil. Mix to get efficient turnover.
2. Once dissolved add the tocopherol phosphate mixture once the internal temperature reaches 57.9-61° C. mix at this temperature till contents melted.
3. Once all contents dissolved allow solution to cool to 32-35° C. add temperature sensitive ingredients (ethanol, retinoids, hydrophobically modified ascorbic acid) and ensure complete dissolution, creating Phase A.
4. In a separate kettle equipped with a propeller blade Phase B was prepared by heating water, water soluble ingredients, and tromethamine to 38-40° C. Mix thoroughly.
5. With effective turnover, add Phase A into Phase B (38-40° C., or at 38.7° C.), mix 20 min
6. In a separate weigh boat disperse Xanthan Gum into Glycerin (Phase C) and carefully transfer this slurry into the mix above.
7. Turn off the heat and mix till solution reaches room temperature.

Process 2:
1. In a side kettle on a hot plate heat DMI, pentylene glycol, and hydrophobic amino acid to 60-65° C. with stir bar. Cover beaker with foil. Mix to get efficient turnover.
2. Once dissolved add the tocopherol phosphate mixture once the internal temperature reaches 57.9-61° C. mix at this temperature till contents melted.
3. Once all contents dissolved allow solution to cool to 32-35° C. add temperature sensitive ingredients (ethanol, retinoids, hydrophobically modified ascorbic acid) and ensure complete dissolution, creating Phase A.
4. In a separate kettle equipped with a propeller blade Phase B was prepared by heating water and water-soluble ingredients to 38-40° C. Mix thoroughly.
5. With effective turnover, add Phase A into Phase B (38-40° C., or at 38.7° C.), mix 20 min
6. Add tromethamine
7. In a separate weigh boat disperse Xanthan Gum into Glycerin (Phase C) and carefully transfer this slurry into the mix above.
8. Turn off the heat and mix till solution reaches room temperature.

Process 3:
1. In a side kettle on a hot plate heat DMI, pentylene glycol, and hydrophobic amino acid to 60-65° C. with stir bar. Cover beaker with foil. Mix to get efficient turnover.
2. Once dissolved add the tocopherol phosphate mixture once the internal temperature reaches 57.9-61° C. mix at this temperature till contents melted.
3. Once all contents dissolved allow solution to cool to 32-35° C. add temperature sensitive ingredients (retinoids, hydrophobically modified ascorbic acid) and ensure complete dissolution. Note no ethanol was added in this process.
4. In a separate kettle equipped with a propeller blade Phase B was prepared by heating water and water-soluble ingredients to 38-40° C. Mix thoroughly.
5. With effective turnover, add Phase A into Phase B (38-40° C., or at 38.7° C.), mix 20 min
6. Add tromethamine
7. In a separate weigh boat disperse Xanthan Gum into Glycerin (Phase C) and carefully transfer this slurry into the mix above.
8. Turn off the heat and mix till solution reaches room temperature.

Process 3 resulted in unwanted precipitates.

Process 4:
1. In a side kettle on a hot plate heat DMI, pentylene glycol, and hydrophobic amino acid to 60-65° C. with stir bar. Cover beaker with foil. Mix to get efficient turnover.
2. Once dissolved add the tocopherol phosphate mixture once the internal temperature reaches 57.9-61° C. mix at this temperature till contents melted.
3. Once all contents dissolved allow solution to cool to 32-35° C. add temperature sensitive ingredients (retinoids, hydrophobically modified ascorbic acid) and ensure complete dissolution.
4. In a separate kettle equipped with a propeller blade Phase B was prepared by heating water, add water-soluble ingredients to 38-40° C. Mix well.
5. With effective turnover, add Phase A into Phase B (38-40° C., or at 38.7° C.), mix 20 min
6. Add ethanol followed by tromethamine
7. In a separate weigh boat disperse Xanthan Gum into Glycerin (Phase C) and carefully transfer this slurry into the mix above.
8. Turn off the heat and mix till solution reaches room temperature.

Process 4 resulted in unwanted precipitates.

Process 5:
1. In a side kettle on a hot plate heat DMI, pentylene glycol, and hydrophobic amino acid to 60-65° C. with stir bar. Cover beaker with foil. Mix to get efficient turnover.
2. Once dissolved add the tocopherol phosphate mixture once the internal temperature reaches 57.9-61° C. mix at this temperature till contents melted.
3. Once all contents dissolved allow solution to cool to 32-35° C. add temperature sensitive ingredients (retinoids, hydrophobically modified ascorbic acid) and ensure complete dissolution.
4. Using a Silverson set at 4000 RPM in a separate kettle Phase B was prepared with water, water-soluble ingredients to were heated to 38-40° C.
5. Phase A was added into Phase B (38-40° C.-at 38.7° C.), mixed 4000 RPM for 20 min
6. Add tromethamine
7. Add ethanol mix 4650 RPM 20 min.
7. In a separate weigh boat disperse Xanthan Gum into Glycerin (Phase C) and carefully transfer this slurry into the mix above, with Silverson at 1300 RPM, drop to 500 RPM until the solution reaches room temperature.
8. Turn off the heat and mix till solution reaches room temperature.

Process 5 resulted in unwanted precipitates.

Process 6:

1. In a side kettle on a hot plate heat DMI, pentylene glycol, and hydrophobic amino acid to 60-65° C. with stir bar. Cover beaker with foil. Mix to get efficient turnover.
2. Once dissolved add the tocopherol phosphate mixture once the internal temperature reaches 57.9-61° C. mix at this temperature till contents melted.
3. Once all contents dissolved allow solution to cool to 32-35° C. add temperature sensitive ingredients (retinoids, hydrophobically modified ascorbic acid) and ensure complete dissolution.
4. Using a Silverson set at 4650 RPM in a separate kettle Phase B was prepared with water, water-soluble ingredients to were heated to 38-40° C.
5. Phase A was added into Phase B (38-40° C. at 38.7° C.), followed by ethanol mixed 4650 RPM 2 min.
6. Switch to slow propeller mixing, add ethanol followed by tromethamine
7. In a separate weigh boat disperse Xanthan Gum into Glycerin (Phase C) and carefully transfer this slurry into the mix above.
8. Turn off the heat and mix till solution reaches room temperature.

Process 6 resulted in unwanted precipitates.

Example 5: Neck Cream Formulations

TABLE 7

Neck Cream Formulation A

| Role | INCI Name (Mixed) | % |
|---|---|---|
| Elastomer | DIMETHICONE/VINYL DIMETHICONE CROSSPOLYMER | 0.10 |
| Emollient | JOJOBA ESTERS CYCLOPENTASILOXANE *HELIANTHUS ANNUUS* (SUNFLOWER) SEED WAX CAPRYLIC/CAPRIC TRIGLYCERIDE *ACACIA DECURRENS* FLOWER CERA (*ACACIA DECURRENS* FLOWER WAX) * POLYGLYCERIN-3 | 5.12 |
| Emulsifier or Surfactant | OCTYLDODECYL XYLOSIDE PEG-30 DIPOLYHYDROXYSTEARATE POLYSORBATE 80 SORBITAN OLEATE | 1.13 |
| gellant | ACRYLAMIDE/SODIUM ACRYLOYLDIMETHYLTAURATE COPOLYMER SODIUM POLYACRYLATE | 1.1 |
| preservative, antioxidant, chelator, filler | HYDROXYACETOPHENONE ETHYLHEXYLGLYCERIN SODIUM PHYTATE XYLOSE | 0.85 |
| solvent | WATER/AQUA/EAU OCTYLDODECANOL ISOHEXADECANE | 71.70 |
| TPM - Ex. 1 (Table 1) | TPM - Ex. 1 (Table 1) | 20.0 |
| | Total | 100.0 |

TABLE 8

Neck Cream Formulation B

| Role | INCI Name (Mixed) | % |
|---|---|---|
| Elastomer | POLYSILICONE-11 | 0.2 |
| Emollient | DIMETHICONE ISONONYL ISONONANOATE CETYL ETHYLHEXANOATE *BUTYROSPERMUM PARKII* (SHEA) BUTTER *HELIANTHUS ANNUUS* (SUNFLOWER) SEED OIL | 17.88 |
| Emulsifier | CETEARYL ALCOHOL C14-22 ALCOHOLS GLYCERYL GLUCOSIDE CETEARYL GLUCOSIDE POTASSIUM CETYL PHOSPHATE C12-20 ALKYL GLUCOSIDE BIS-PEG-12 DIMETHICONE LECITHIN DECYL GLUCOSIDE CETEARETH-25 CETYL ALCOHOL BEHENIC ACID | 6.64 |
| Functional | 3-O-ETHYL ASCORBIC ACID NIACINAMIDE RETINYL PALMITATE HYDROXYAPATITE WHEY PROTEIN *PYRUS MALUS* (APPLE) FRUIT EXTRACT CALCIUM PCA MAGNESIUM PCA RETINAL SEA SALT/MARIS SAL/SEL MARIN ADENOSINE CERAMIDE NP CHOLESTEROL CERAMIDE NS CERAMIDE AP CERAMIDE EOP CERAMIDE EOS CAPROOYL PHYTOSPHINGOSINE CAPROOYL SPHINGOSINE ASCORBYL PALMITATE TOCOPHEROL | 0.72 |
| Gellant | CARBOMER CETYL HYDROXYETHYLCELLULOSE GELLAN GUM | 0.32 |
| Humectant | GLYCERIN DIGLYCERIN SODIUM ACETYLATED HYALURONATE PENTYLENE GLYCOL SODIUM HYALURONATE | 4.48 |
| pH adjuster | TROMETHAMINE Exceeds maximum authorized by the brand (0.000000%) LACTIC ACID DISODIUM PHOSPHATE | 0.34 |
| preservative, antioxidant, chelator, filler, film former, fragrance | PHENOXYETHANOL HDI/TRIMETHYLOL HEXYLLACTONE CROSSPOLYMER LACTOSE ETHYLHEXYLGLYCERIN DISODIUM EDTA MINERAL SALTS GLUCOSE CAPRYLYL GLYCOL SILICA HEXYLENE GLYCOL SODIUM BENZOATE FRAGRANCE/PARFUM BHT Exceeds maximum authorized by the brand (0.000000%) HYDRATED SILICA SILICA DIMETHYL SILYLATE | 1.96 |

TABLE 8-continued

Neck Cream Formulation B

| Role | INCI Name (Mixed) | % |
|---|---|---|
| solvent | WATER/AQUA/EAU ALCOHOL DENAT. | 47.46 |
| TPM Phase Ex. 2 (Table 1) | TPM Phase Ex. 2 | 20.0 |
| | total | 100.0 |

TABLE 9

Neck Cream Formulation C

| Role | INCI Name (mixed) | % |
|---|---|---|
| elastomer | POLYSILICONE-11 | 0.2 |
| emollient | DIMETHICONE<br>ISONONYL ISONONANOATE<br>CETYL ETHYLHEXANOATE<br>*BUTYROSPERMUM PARKII* (SHEA) BUTTER<br>*HELIANTHUS ANNUUS* (SUNFLOWER) SEED OIL | 17.88 |
| emulsifier | CETEARYL ALCOHOL<br>C14-22 ALCOHOLS<br>GLYCERYL GLUCOSIDE<br>CETEARYL GLUCOSIDE<br>POTASSIUM CETYL PHOSPHATE<br>C12-20 ALKYL GLUCOSIDE<br>BIS-PEG-12 DIMETHICONE<br>COCO-GLUCOSIDE<br>LECITHIN<br>DECYL GLUCOSIDE<br>CETEARETH-25<br>CETYL ALCOHOL<br>BEHENIC ACID | 6.72 |
| Other Functional ingredients | 3-O-ETHYL ASCORBIC ACID<br>NIACINAMIDE<br>RETINYL PALMITATE<br>HYDROXYAPATITE<br>*PYRUS MALUS* (APPLE) FRUIT EXTRACT<br>CALCIUM PCA<br>MAGNESIUM PCA<br>RETINAL<br>SEA SALT/MARIS SAL/SEL MARIN<br>GLAUCINE<br>ADENOSINE<br>CERAMIDE NP<br>CHOLESTEROL<br>CERAMIDE NS<br>CERAMIDE AP<br>CERAMIDE EOP<br>CERAMIDE EOS<br>CAPROOYL PHYTOSPHINGOSINE<br>CAPROOYL SPHINGOSINE<br>ASCORBYL PALMITATE | 0.66 |
| Gellant | CARBOMER<br>CETYL HYDROXYETHYLCELLULOSE<br>GELLAN GUM | 0.32 |
| humectant | GLYCERIN<br>DIGLYCERIN<br>SODIUM ACETYLATED HYALURONATE<br>PENTYLENE GLYCOL<br>SODIUM HYALURONATE | 7.73 |
| pH adjuster | TROMETHAMINE<br>SODIUM CITRATE<br>CITRIC ACID<br>LACTIC ACID<br>DISODIUM PHOSPHATE | 0.32 |
| preservative, antioxidant, chelator, filler, film former, fragrance | PHENOXYETHANOL<br>ACRYLATES COPOLYMER<br>HDI/TRIMETHYLOL HEXYLLACTONE CROSSPOLYMER<br>ETHYLHEXYLGLYCERIN<br>DISODIUM EDTA<br>CAPRYLYL GLYCOL<br>VP/POLYCARBAMYL POLYGLYCOL ESTER<br>HYDROLYZED SESAME PROTEIN PG-PROPYL METHYLSILANEDIOL<br>GLUCOSE<br>SILICA<br>HEXYLENE GLYCOL<br>SODIUM BENZOATE<br>BHT<br>HYDRATED SILICA<br>SILICA DIMETHYL SILYLATE<br>TOCOPHEROL<br>FRAGRANCE/PARFUM | 2.36 |
| solvent | WATER/AQUA/EAU ALCOHOL DENAT. ALCOHOL | 63.8 |
| TPM Phase - Ex. 2 (Table 1) | TPM Phase - Ex. 2 (Table 1) | 20.0 |
| | total | 100 |

TABLE 10

Neck Cream Formulation D

| Role | INCI Name (Mixed) | % |
|---|---|---|
| Elastomer | POLYSILICONE-11 | 0.20 |
| Emollient | DIMETHICONE<br>ISONONYL ISONONANOATE<br>CETYL ETHYLHEXANOATE<br>*BUTYROSPERMUM PARKII* (SHEA) BUTTER<br>*HELIANTHUS ANNUUS* (SUNFLOWER) SEED OIL | 17.88 |
| Emulsifier | CETEARYL ALCOHOL<br>C14-22 ALCOHOLS<br>GLYCERYL GLUCOSIDE<br>CETEARYL GLUCOSIDE<br>POTASSIUM CETYL PHOSPHATE<br>C12-20 ALKYL GLUCOSIDE<br>BIS-PEG-12 DIMETHICONE<br>COCO-GLUCOSIDE<br>LECITHIN<br>DECYL GLUCOSIDE<br>CETEARETH-25<br>CETYL ALCOHOL<br>BEHENIC ACID | 6.72 |
| Functional | 3-O-ETHYL ASCORBIC ACID<br>NIACINAMIDE<br>RETINYL PALMITATE<br>HYDROXYAPATITE<br>*PYRUS MALUS* (APPLE) FRUIT EXTRACT<br>CALCIUM PCA<br>MAGNESIUM PCA<br>RETINAL<br>SEA SALT/MARIS SAL/SEL MARIN<br>GLAUCINE<br>ADENOSINE<br>CERAMIDE NP<br>CHOLESTEROL<br>CERAMIDE NS<br>CERAMIDE AP<br>CERAMIDE EOP<br>CERAMIDE EOS<br>CAPROOYL PHYTOSPHINGOSINE<br>CAPROOYL SPHINGOSINE<br>ASCORBYL PALMITATE | 0.66 |
| Gellant | CARBOMER<br>CETYL HYDROXYETHYLCELLULOSE<br>GELLAN GUM | 0.32 |

TABLE 10-continued

Neck Cream Formulation D

| Role | INCI Name (Mixed) | % |
|---|---|---|
| Humectant | GLYCERIN<br>DIGLYCERIN<br>SODIUM ACETYLATED HYALURONATE<br>PENTYLENE GLYCOL<br>HEXYLENE GLYCOL<br>SODIUM HYALURONATE | 5.98 |
| pH adjuster | TROMETHAMINE<br>SODIUM CITRATE<br>CITRIC ACID<br>LACTIC ACID<br>DISODIUM PHOSPHATE | 0.32 |
| Preservative,<br>antioxidant,<br>fragrance,<br>or filler | TOCOPHEROL<br>PHENOXYETHANOL<br>ETHYLHEXYLGLYCERIN<br>DISODIUM EDTA<br>CAPRYLYL GLYCOL<br>SODIUM BENZOATE<br>FRAGRANCE/PARFUM<br>BHT<br>HDI/TRIMETHYLOL HEXYLLACTONE<br>CROSSPOLYMER<br>GLUCOSE<br>SILICA<br>HYDRATED SILICA<br>SILICA DIMETHYL SILYLATE | 1.61 |
| solvent | WATER/AQUA/EAU<br>ALCOHOL DENAT.<br>ALCOHOL | 46.30 |
| TPM - Ex. 2<br>(Table 1) | TPM - Ex. 2<br>(Table 1) | 20.0 |
| | Total | 100.0 |

TABLE 11

Neck Cream Formulation E

| role | INCI Name (Mixed) | % |
|---|---|---|
| Elastomer | POLYSILICONE-11 | 0.33 |
| Emollient | DIMETHICONE<br>ISONONYL ISONONANOATE | 15.67 |
| Emulsifier | CETEARYL ALCOHOL<br>C14-22 ALCOHOLS<br>CETEARYL GLUCOSIDE<br>POTASSIUM CETYL PHOSPHATE<br>C12-20 ALKYL GLUCOSIDE<br>COCO-GLUCOSIDE | 5.8 |
| Functional | GLYCERYL GLUCOSIDE<br>RETINYL PALMITATE<br>3-O-ETHYL ASCORBIC ACID<br>NIACINAMIDE<br>HYDROXYAPATITE<br>RETINAL<br>GLAUCINE | 1.51 |
| Gellant | CARBOMER<br>SODIUM POLYACRYLOYLDIMETHYL TAURATE | 0.43 |
| Humectant | GLYCERIN<br>PENTYLENE GLYCOL<br>SODIUM ACETYLATED HYALURONATE | 5.7 |
| pH adjuster | SODIUM HYDROXIDE<br>SODIUM CITRATE<br>CITRIC ACID | 0.12 |
| preservative,<br>antioxidant,<br>chelator,<br>filler,<br>film former,<br>fragrance | PHENOXYETHANOL<br>HDI/TRIMETHYLOL HEXYLLACTONE<br>CROSSPOLYMER<br>FRAGRANCE/PARFUM<br>ETHYLHEXYLGLYCERIN<br>DISODIUM EDTA<br>CAPRYLYL GLYCOL<br>GLUCOSE<br>SILICA<br>TOCOPHEROL<br>LIMONENE<br>LINALOOL | 1.66 |
| Solvent | WATER/AQUA/EAU<br>ALCOHOL DENAT. | 58.77 |
| TPM Phase<br>Ex. 9<br>(Table 2) | WATER/AQUA/EAU<br>DIMETHYL ISOSORBIDE<br>GLYCERIN<br>PENTYLENE GLYCOL<br>TOCOPHERYL PHOSPHATE MIXTURE<br>DIPALMITOYL HYDROXYPROLINE<br>3-O-CETYL ASCORBIC ACID<br>ARGININE<br>XANTHAN GUM<br>ALCOHOL<br>25% SODIUM HYDROXIDE | 10.0 |
| | TOTAL | 100.0 |

Example 6: TPM Penetration and Permeation

Figure 2:
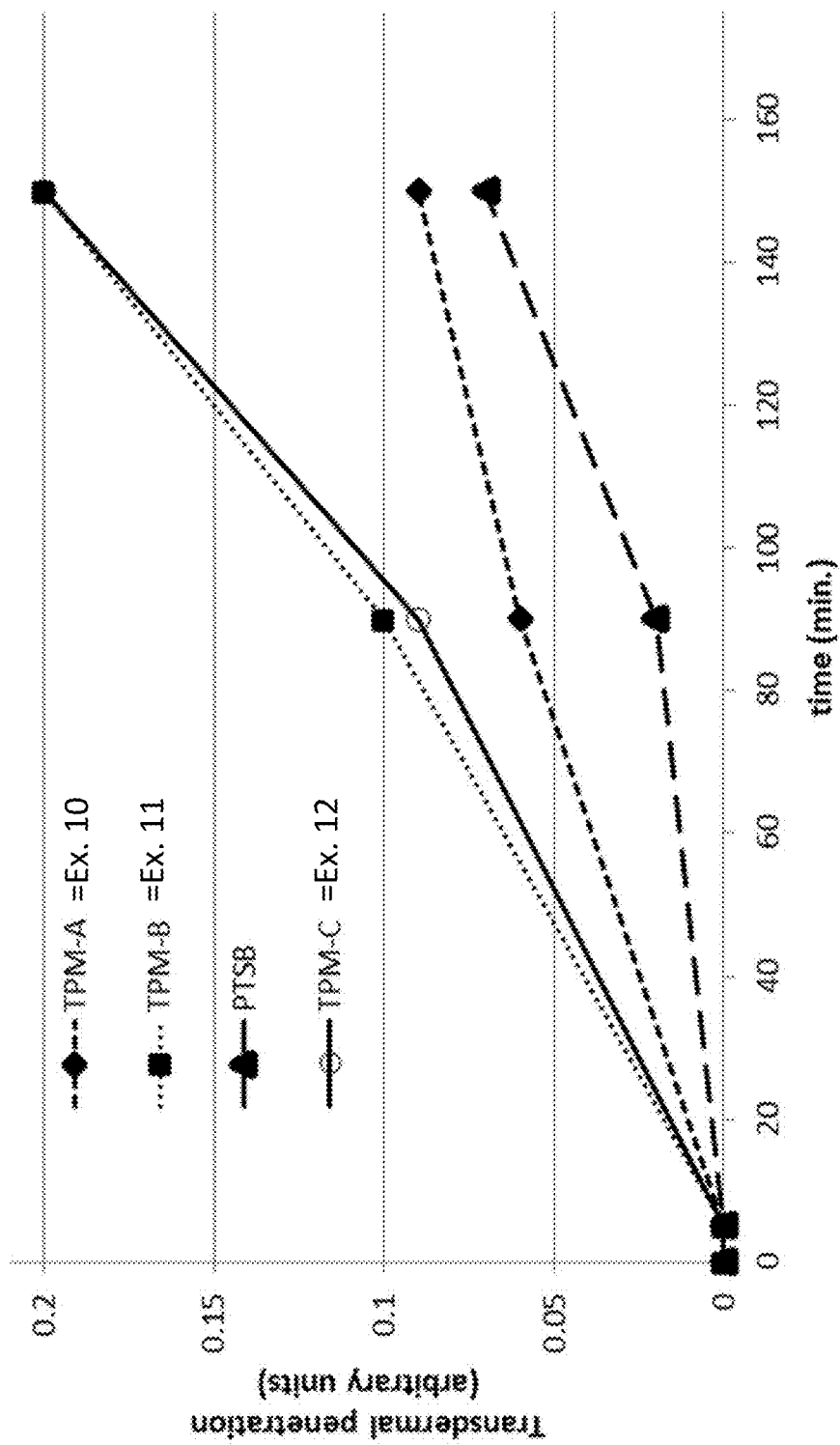
FIG. 2 demonstrates the transdermal penetration of 0.5% resveratrol dimethyl ether prepared in the 4 test samples.

Experiments were performed to mimic transdermal and intradermal delivery using a skin-like Strat-M Membrane Model. The samples tested (see Tables 12, and 13) included: Ex. 10, Ex. 11, Ex. 12, and PTSB (a 0.5% resveratrol dimethyl ether solution in capric/caprylic triglycerides). FIG. 2 demonstrated the transdermal penetration of 0.5% resveratrol dimethyl ether through the 4 test samples. Quantified by UV/Vis @321 nm.

TABLE 12

Compositions of Inventive compositions Ex. 10 and Ex. 11 formulations tested

| Phase | Role | INCI | Ex. 10 | Ex. 11 |
|---|---|---|---|---|
| B | Solvent, probe ingredient and preservative | Pterostilbene<br>water<br>Sodium benzoate | 0.5<br>75.5 | 0.5<br>75.5 |
| A | Emollient | Dicapryl ether<br>Octyldodecanol<br>Squalene<br>Caprylic/Capric Triglyceride | 11.0 | 11.0 |
| | Functional | Tocopherol phosphate mixture | 0 | 1.0 |
| | Emulsifier | Glyceryl Stearate and PEG-100 Stearate<br>Polyglyceryl-10 Laurate | 3.0 | 1.0 |
| | Water soluble ingredient | Lecithin in a polyol | 0 | 1.0 |
| C | Gellant | 3% XANTHAN GUM solution | 10.0 | 10.0 |

TABLE 13

Compositions of inventive composition Ex. 12 neat formulations tested

| Phase | Role | INCI | Ex. 12 |
|---|---|---|---|
| A | Solvent | Dimethyl isosorbide<br>Pentylene glycol | 10.0 (1:9 ratio) |
| | TPM | Tocopherol phosphate | 2.0 |
| | Probe ingredient | Pterostilbene 99% | 0.5 |

TABLE 13-continued

Compositions of inventive composition
Ex. 12 neat formulations tested

| Phase | Role | INCI | Ex. 12 |
|---|---|---|---|
| B | Alcohol | Ethanol | 8.0 |
| C | Water phase base | Water | 79.30 |
| | | Sodium Benzoate | 0.2 |

Figure 3:
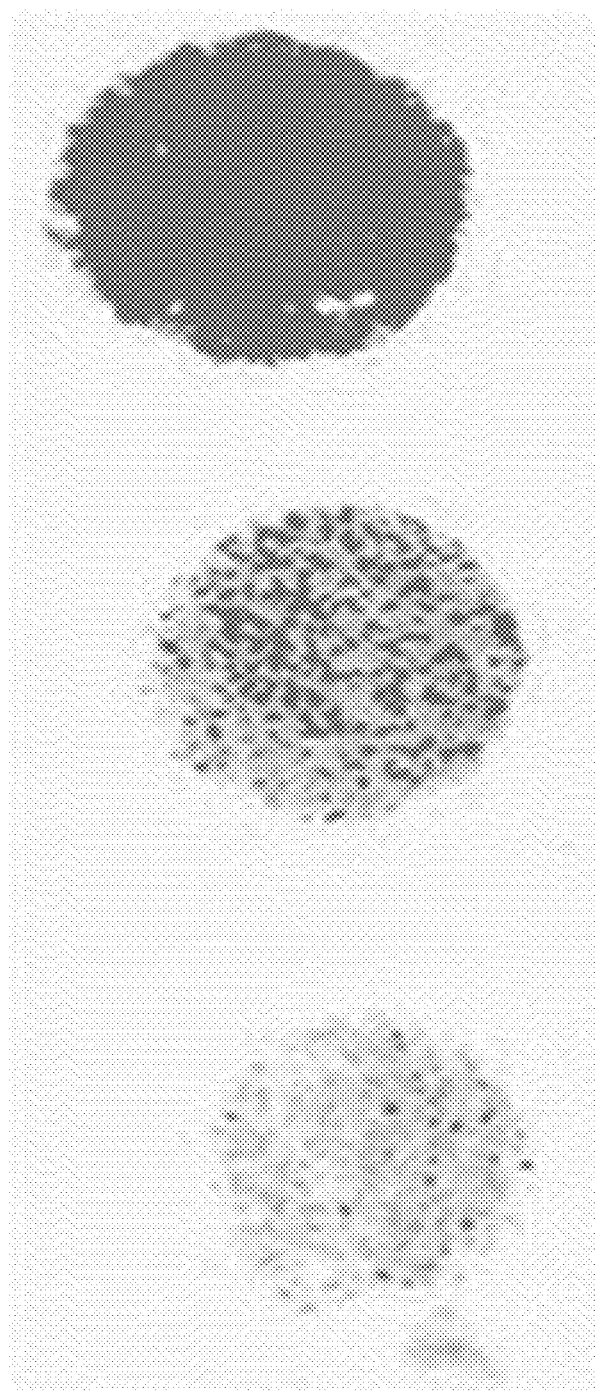
FIG. 3 demonstrates the time-course permeation of resveratrol dimethyl ether through a Strat-M Membrane using illumination with UVB light after 0.5 min., 5 min. and 15 min.

Time-course permeation of resveratrol dimethyl ether was tested using TPM mini-emulsions through a Strat-M Membrane. FIG. 3 demonstrates the illumination with UVB light after 0.5 min, 5 min and 15 min (from left to right).

Figure 4:
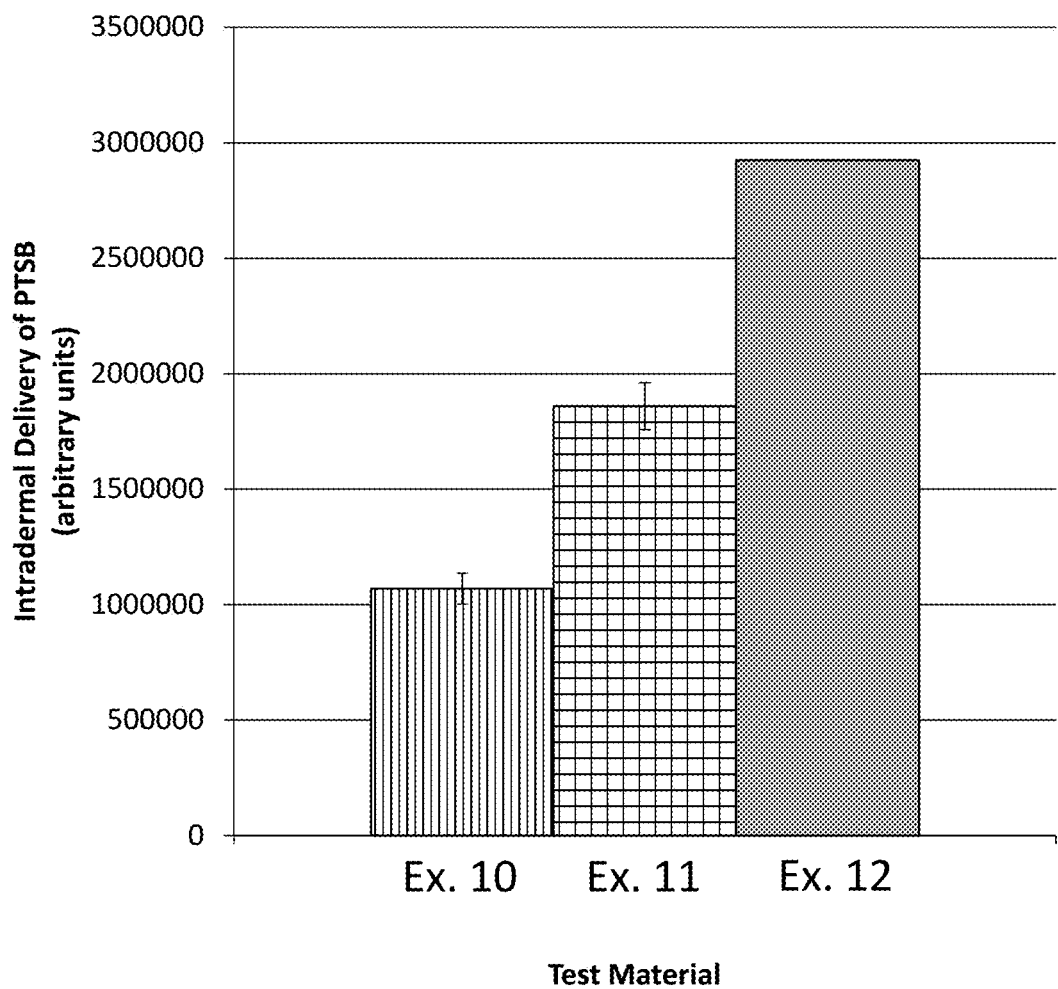
FIG. 4 shows the results of tests performed to demonstrate resveratrol dimethyl ether permeation into Strat-M membranes.

Tests were performed to demonstrate resveratrol dimethyl ether permeation into Strat-M membranes from Ex. 10, Ex. 11 and Ex. 12, see FIG. 4.

Example 7: TPM Formulations vs. Commercial Vesicles/Liposomes

Free radical scavenging activity was tested of different experimental conditions expressed as % water control. The positive control, ascorbic acid (Ref. 5), reached the expected level of inhibitory activity technically validating the experiments.

Formulations tested: Ref. 2 is a commercially available liposome containing (RonaCare®): Water, Hydrogenated Lecithin, Dipalmitoyl Hydroxyproline, Lecithin, Phenoxyethanol, Mannitol, Beta-Sitosterol, Linoleic Acid, Tocopherol, and Sodium Ascorbate. Ref. 3 is a commercially available composition containing Water, Alcohol, Lecithin, Disodium Rutinyl Disulfate, Hydroxyproline, Sorbitol, Magnesium Ascorbyl Phosphate, Tocopherol, Ascorbyl Palmitate, Glyceryl Stearate, Glyceryl Oleate, and Citric Acid. Ex. 1 see Table 1 above.

See Table 14 for results.

TABLE 14

Free Radical Scavenging Activity

| Test Material | ABTS (% Control) | p value |
|---|---|---|
| H2O | 100 | 1 |
| Ref. 5 @ 0.06 mg/mL | 0 | |
| Ref. 2 @ 3% | 80 | 0.000 |
| Ref. 2 @ 0.3% | 85 | 0.000 |
| Ref. 3 @ 3% | 13 | 0.000 |
| Ref. 3 @ 0.3% | 73 | 0.000 |
| Ex. 1 @ 3% | 7 | 0.000 |
| Ex. 1 @ 0.3% | 15 | 0.000 |

Example 8: Test of Melanin Content

Tests were performed to demonstrate the effect of different experimental conditions on the melanin content in human epidermal melanocytes. Test materials were added to exponentially growing cultures and the experiment was terminated 7 days later.

Formulations tested: Ref. 2 is a commercially available liposome containing (RonaCare®): Water, Hydrogenated Lecithin, Dipalmitoyl Hydroxyproline, Lecithin, Phenoxyethanol, Mannitol, Beta-Sitosterol, Linoleic Acid, Tocopherol, and Sodium Ascorbate. Ref. 3 is a commercially available composition containing Water, Alcohol, Lecithin, Disodium Rutinyl Disulfate, Hydroxyproline, Sorbitol, Magnesium Ascorbyl Phosphate, Tocopherol, Ascorbyl Palmitate, Glyceryl Stearate, Glyceryl Oleate, and Citric Acid. Ref. 4 is a commercially available composition of Kojic acid. Ex. 1 see Table 1 above. N/A: data not reported due to the low cell count.

See Table 15. Demonstrates the compositions ability to address pigmentation in décolletage.

TABLE 15

Melanin content

| Test Material | % Control (Melanin) cell number-adjusted | p value |
|---|---|---|
| H2O | 100 | 1 |
| Ref. 2 @ 500 ug/mL | 88 | 0.076 |
| Ref. 2 @ 100 ug/mL | 122 | 0.024 |
| Ref. 3 @ 500 ug/mL | N/A | N/A |
| Ref. 3 @ 100 ug/mL | 75 | 0.008 |
| Ex. 1 @ 500 ug/mL | 69 | 0.004 |
| Ex. 1@ 100 ug/mL | 82 | 0.036 |
| Ref. 4 @ 200 ug/mL | 46 | 0.013 |
| Ref. 4 @ 50 ug/mL | 103 | 0.634 |

Example 9: Efficacy Evaluation of TPM Containing Neck Cream

Purpose: An efficacy evaluation of a Neck Cream featuring mixed Tocopheryl Phosphates (TPM) as an encapsulated delivery system for multiple cosmetic ingredients.

Study Design: A study of 15 consenting men and women was performed at the Rodan and Fields Skin Research Center in San Ramon, California. Subjects were given an experimental neck cream and advised to apply product in the morning (before sunscreen), and evening without applying any other products to their necks other than sunscreen during the day. At the time points of 4, 8, and 12 Weeks Ultrasound Intensity Scores of impacted areas were measured using Cortex DermaLab Ultrasound module, operating at 10-20 MHz.

Results: At each measurement interval the skin density scores of each subject were measured and tabled using relative Ultrasound Intensity Score, see Table 16.

TABLE 16

Ultrasound Intensity Score- all subjects treated
with Neck Cream Formulation B (Table 8)

| Subject | Baseline | Week 4 | Week 8 | Week 12 |
|---|---|---|---|---|
| 1 | 24.33 | 25.27 | 28.63 | 24.80 |
| 2 | 30.33 | 44.43 | 39.17 | 31.43 |
| 3 | 31.67 | 38.60 | 40.00 | 40.00 |
| 4 | 37.20 | 48.37 | 48.47 | 44.10 |
| 5 | 36.23 | 34.27 | 48.37 | 45.00 |
| 6 | 33.37 | 39.10 | 50.77 | 45.77 |
| 7 | 41.40 | 39.40 | 45.23 | 45.80 |
| 8 | 39.80 | 51.80 | 59.53 | 47.87 |
| 9 | 39.67 | 43.67 | 53.93 | 48.03 |
| 10 | 48.10 | 51.30 | 54.67 | 51.70 |
| 11 | 40.10 | 34.73 | 56.70 | 55.40 |
| 12 | 29.83 | 51.70 | 48.30 | 55.90 |
| 13 | 44.50 | 40.30 | 45.07 | 58.50 |
| 14 | 55.17 | 44.13 | 64.70 | 60.17 |
| 15 | 57.20 | 63.33 | 75.87 | 70.70 |
| Mean | 39.26 | 43.36 | 50.63 | 48.34 |
| Mean % Change from Baseline | — | 10% | 29% | 23% |

TABLE 16-continued

Ultrasound Intensity Score- all subjects treated with Neck Cream Formulation B (Table 8)

| Subject | Baseline | Week 4 | Week 8 | Week 12 |
|---|---|---|---|---|
| % of Subjects Illustrating Improvement | — | 67% | 100% | 100% |

Discussion: The Ultrasound Intensity Score illustrates changes in the density of the tissue under the epidermal layer. The intensity score illustrates novel growth and cell proliferation, as opposed to dormant pockets. The novel neck cream featuring Tocopheryl Phosphate (TPM) encapsulated technology, had illustrated a clear difference in dermal cellular activity, and thus illustrates promise in an anti-aging neck cream, designed to target the look of fine lines and wrinkles often caused by lack of cellular support. While roughly ⅔ of the panelists showed improvement from baseline at week 4, by week 8 all subjects illustrated improvements from baseline. Furthermore this trend continued all the way until week 12. The magnitude of improvement is illustrated by the mean percent change from baseline. The mean score stared with a 10% increase at week 4, and had peaked at week 8 with a 29% improvement from baseline. Eventually this mean percent increase leveled off to 23% improvement from baseline. This illustrates a strong positive change from baseline, and relatively consistent results with ongoing product usage. The dip in efficacy from week 8 to week 12 may have been related to the summer months, and subject exposure to the warmer, and sunnier environment.

Conclusion: The neck cream utilizing Tocopheryl Phosphates (TPM) illustrated clear performance benefits, and illustrated strong dermal penetration of cosmetic ingredients.

The disclosures of each and every patent, patent application, publication, and accession number cited herein are hereby incorporated herein by reference in their entirety.

While present disclosure has been disclosed with reference to various embodiments, it is apparent that other embodiments and variations of these may be devised by others skilled in the art without departing from the true spirit and scope of the disclosure. The appended claims are intended to be construed to include all such embodiments and equivalent variations.

The invention claimed is:

1. A method for preparing a tocopherol phosphate mixture (TPM) liposomal composition comprising:
   a) mixing a lipophilic ingredient with a polar solvent system and heating the resulting mixture to a temperature of at least about 60° C.;
   b) adding a mixture of tocopherol phosphate derivative ingredients to the mixture from step a) once temperature reaches about 57.9° C. and maintaining the temperature sufficient to melt all contents, wherein the mixture of tocopherol phosphate derivative ingredients are selected from alpha-tocopheryl phosphate (TP), di-alpha-tocopheryl phosphate (T2P), beta tocopherol phosphate, gamma tocopherol phosphate, delta tocopherol phosphate, or a combination thereof;
   c) cooling the mixture from step b) to a temperature of about 32° C. to about 35° C., adding one or more lipophilic ingredients and ethanol into the cooled mixture, and mixing the mixture until complete dissolution to form Phase A;
   d) mixing, in a separate container, one or more water soluble ingredients, and water thoroughly at a temperature of about 38° C. to about 40° C. to form Phase B;
   e) adding Phase A into Phase B and mixing at a temperature of about 38° C. to about 40° C. for at least 20 minutes;
   f) adding a neutralizing base to the mixture of step e);
   g) dispersing xanthan gum into glycerin to form Phase C and mixing Phase C into the mixture of step f); and
   h) turning off the heat to the mixture of step g) and stirring the mixture until the temperature of the mixture reaches room temperature, thereby forming the TPM liposomal composition.

2. The method of claim 1, wherein the polar solvent system comprises a polar solvent 1 and a polar solvent 2 each selected from the group consisting of a polyol, a mono-isosorbide ether, a di-alkyl isosorbide ether, and combinations thereof.

3. The method of claim 2, wherein the polar solvent 1 is a polyol and the polar solvent 2 is a di-alkyl isosorbide ether.

4. The method of claim 3, wherein the polyol is pentylene glycol and the di-alkyl isosorbide ether is dimethyl isosorbide (DMI).

5. The method of claim 2, wherein the polar solvent 1 is present in an amount of about 5% to about 10% by weight of the TPM liposomal composition and the polar solvent 2 is present in an amount of about 2% to about 6% by weight of the TPM liposomal composition.

6. The method of claim 1, wherein the ethanol is about 5% to about 10% by weight of the TPM liposomal composition.

7. The method of claim 1, wherein the mixture of tocopherol phosphate derivative ingredients is a mixture of TP and T2P.

8. The method of claim 7, wherein the mixture of TP and T2P is in a ratio of about 4:1 to about 1:1 (TP:T2P).

9. The method of claim 1, wherein the mixture of tocopherol phosphate derivative ingredients is about 1.5% to about 5% by weight of the TPM liposomal composition.

10. The method of claim 1, wherein the neutralizing base is about 0.1% to about 1% by weight of the TPM liposomal composition.

11. The method of claim 1, wherein the neutralizing base is tromethamine or sodium hydroxide.

12. The method of claim 1, wherein the temperature of step a) is about 60° C. to about 65° C.

13. The method of claim 1, wherein the temperature of step b) is about 57.9° C. to about 61° C.

14. The method of claim 1, wherein the one or more lipophilic ingredients is selected from the group consisting of a hydrophobically modified amino acid, a hydrophobically modified vitamin, a retinoid, a resveratrol derivative, a fatty acid, a fatty ester, and combinations thereof.

15. The method of claim 14, wherein the hydrophobically modified amino acid is hydrophobically modified proline, wherein the hydrophobically modified proline is dipalmitoyl hydroxyproline, and wherein the hydrophobically modified vitamin is a hydrophobically modified ascorbic acid.

16. The method of claim 14, wherein the retinoid is selected from the group consisting of retinaldehyde, ester of retinoic acid, retinyl palmitate, alitretinoin (9-cis-retinoic acid), tretinoin (all-trans-retinoic acid), isotretinoin (13-cis-retinoic acid), etretinate, acitretin, adapalene, bexarotene, tazarotene, hydroxypinacolone retinoate, and combinations thereof.

17. The method of claim 14, wherein the fatty ester is a blend of pterostilbene (resveratrol dimethyl ether) and xymenynic acid dissolved in glyceryl linoleate and glyceryl linolenate.

18. The method of claim 1, wherein one or more water soluble ingredients and the water are about 70% to 85% by weight of the TPM liposomal composition.

19. The method of claim 1, wherein the one or more water soluble ingredients is a water soluble amino acid, a water soluble vitamin, xanthine, or combinations thereof.

20. The method of claim 1, wherein the TPM liposomal composition has a pH of about 4.5 to about 5.

* * * * *